United States Patent
Ikeda et al.

(10) Patent No.: US 8,427,470 B2
(45) Date of Patent: Apr. 23, 2013

(54) COMPUTER PRODUCT, INFORMATION DISPLAY APPARATUS, AND INFORMATION DISPLAY METHOD

(75) Inventors: Noriko Ikeda, Kawasaki (JP); Yoshio Nakao, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 49 days.

(21) Appl. No.: 13/137,757

(22) Filed: Sep. 9, 2011

(65) Prior Publication Data
US 2012/0002844 A1      Jan. 5, 2012

Related U.S. Application Data

(63) Continuation of application No. PCT/JP2010/054891, filed on Mar. 19, 2010.

(30) Foreign Application Priority Data

Mar. 27, 2009    (WO) .................. PCT/JP2009/056301

(51) Int. Cl.
*G06T 15/00* (2011.01)
(52) U.S. Cl.
USPC ....................................................... 345/419
(58) Field of Classification Search .................. None
See application file for complete search history.

(56) References Cited

U.S. PATENT DOCUMENTS

| | | | |
|---|---|---|---|
| 6,127,524 A | 10/2000 | Casipit et al. | |
| 6,515,658 B1 | 2/2003 | Endoh | |
| 2004/0170949 A1 | 9/2004 | O'Donoghue et al. | |
| 2006/0028466 A1* | 2/2006 | Zhou et al. ..................... | 345/420 |
| 2009/0006059 A1 | 1/2009 | Arora et al. | |

FOREIGN PATENT DOCUMENTS

| | | |
|---|---|---|
| JP | 2001-22936 | 1/2001 |
| JP | 2002-507882 | 3/2002 |
| JP | 2002-259395 | 9/2002 |
| JP | 2005-507096 | 3/2005 |
| JP | 2009-58499 | 3/2009 |
| WO | 2010/109649 A1 | 9/2010 |

OTHER PUBLICATIONS

Notification Concerning Transmittal of International Preliminary Report on Patentability for International Application PCT/JP2010/054891; PCT/IB326; mailing date Oct. 6, 2011.

(Continued)

*Primary Examiner* — Xiao M. Wu
*Assistant Examiner* — Mohammad H Akhavannik
(74) *Attorney, Agent, or Firm* — Staas & Halsey LLP

(57) ABSTRACT

A 3-dimensional model of an antigen is regarded as a display subject and a 3-dimensional model of an antibody is regarded as a comparison subject. A portion of the molecular surface of the display subject at a distance enabling binding with the comparison subject is cut out as a display surface. The 3-dimensional model of the antigen, which is the display subject, is displayed in a rotated state, where the normal of the display surface is rotated to point in a counter viewing direction, whereby the 3-dimensional model is rotated in a viewing coordinate system. The display surface alone is displayed in color, whereas other portions of the molecular surface are not, thereby enabling the display surface of the antigen that is at a distance enabling binding with the antibody to be displayed at a position easily viewed by the user.

12 Claims, 32 Drawing Sheets

OTHER PUBLICATIONS

International Preliminary Report on Patentability for International Application PCT/JP2010/054891; PCT/IB373; mailing date Sep. 27, 2011.

International Preliminary Report on Patentability for International Application PCT/JP2010/054891; PCT/IB338; mailing date Nov. 24, 2011.

Patent Cooperation Treaty; Written Opinion of the International Authority for International Application PCT/JP2010/054891; PCT/ISA/237; Dated Apr. 13, 2010.

International Search Report for PCT/JP2010/054891, mailed Apr. 13, 2009.

Kengo Kinoshita et al., "eF-site and PDBjViewer: database and viewer for protein functional sites", 2004, Bioinformatics, vol. 20, No. 8, p. 1329-1330.

Michel F. Sanner et al., "Reduced Surface: an Efficient Way to Compute Molecular Surfaces", 1996, Biopolymers, vol. 38(3), p. 305-320.

W. Rocchia et al., "Electrostatic potential calculation for biomolecules—creating a database of pre-calculated values reported on a per residue basis for all PDB protein structures", 2007 Genetics and Molecular Research, 6(4), p. 923-936.

B.Z. Lu et al., "Recent Progress in Numerical Methods for the Poisson-Boltzmann Equation in Biophysical Applications", May 2008, Communications in Computational Physics, vol. 3, No. 5, p. 973-1009.

"Open GL", http://opengl.org/, Mar. 8, 2010, 4pp.

M.A. Larkin et al., "Clustal W and Clustal X version 2.0", 2007, Bioinformatics, vol. 23, No. 21, p. 2947-2948.

Oscar Sverud et al., "Towards optimal views of proteins", 2003, Bioinformatics, vol. 19, No. 7, p. 882-888.

International Search Report for corresponding International Application PCT/JP2009/056301; mailed May 26, 2009.

* cited by examiner

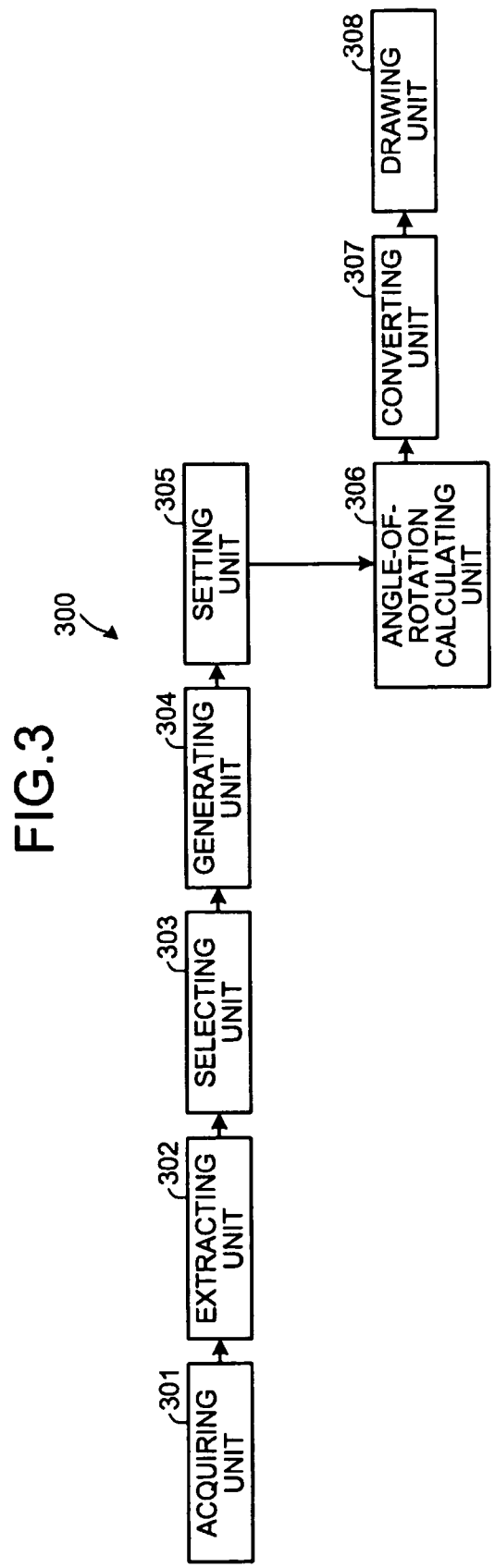

| RECORD TYPE | ATOM ID NUMBER | ATOM NAME | RESIDUE NAME | CHAIN NAME | RESIDUE ID NUMBER | COORDINATES (x, y, z) | | |
|---|---|---|---|---|---|---|---|---|
| ATOM | 1 | N | ASP | A | 1 | 29.242 | 26.159 | 5.769 |
| ATOM | 2 | CA | ASP | A | 1 | 29.854 | 26.753 | 6.983 |
| ATOM | 3 | C | ASP | A | 1 | 29.732 | 25.793 | 8.161 |
| ATOM | 4 | O | ASP | A | 1 | 29.058 | 24.776 | 8.028 |
| ATOM | 5 | CB | ASP | A | 1 | 29.216 | 28.119 | 7.303 |
| ATOM | 6 | CG | ASP | A | 1 | 29.176 | 29.038 | 6.078 |
| ... | | | | | | | | |
| ATOM | 1602 | 1HZ | LYS | A | 107 | 6.100 | 31.520 | 37.966 |
| ATOM | 1603 | 2HZ | LYS | A | 107 | 5.658 | 29.998 | 37.422 |
| ATOM | 1604 | 3HZ | LYS | A | 107 | 6.576 | 31.051 | 36.542 |
| ATOM | 1605 | N | ASP | B | 1 | 40.617 | 54.935 | 25.812 |
| ATOM | 1606 | CA | ASP | B | 1 | 39.490 | 54.006 | 26.084 |
| ATOM | 1607 | C | ASP | B | 1 | 38.386 | 54.250 | 25.067 |
| ATOM | 1608 | O | ASP | B | 1 | 38.198 | 55.396 | 24.676 |
| ATOM | 1609 | CB | ASP | B | 1 | 38.977 | 54.164 | 27.521 |
| ATOM | 1610 | CG | ASP | B | 1 | 40.098 | 53.796 | 28.488 |
| ... | | | | | | | | |
| ATOM | 3349 | 1HB | ALA | B | 114 | 7.725 | 53.127 | 1.211 |
| ATOM | 3350 | 2HB | ALA | B | 114 | 9.364 | 53.352 | 1.878 |
| ATOM | 3351 | 3HB | ALA | B | 114 | 8.145 | 54.630 | 1.995 |
| ATOM | 3352 | N | LYS | C | 1 | 59.677 | 27.152 | 30.431 |
| ATOM | 3353 | CA | LYS | C | 1 | 59.757 | 25.688 | 30.195 |
| ATOM | 3354 | C | LYS | C | 1 | 60.312 | 25.387 | 28.793 |
| ATOM | 3355 | O | LYS | C | 1 | 60.106 | 26.192 | 27.892 |
| ATOM | 3356 | CB | LYS | C | 1 | 58.361 | 25.064 | 30.411 |
| ATOM | 3357 | CG | LYS | C | 1 | 58.271 | 23.593 | 29.978 |
| ... | | | | | | | | |
| ATOM | 5310 | 1HD2 | LEU | C | 129 | 50.507 | 14.949 | 18.503 |
| ATOM | 5311 | 2HD2 | LEU | C | 129 | 50.145 | 14.519 | 20.177 |
| ATOM | 5312 | 3HD2 | LEU | C | 129 | 49.302 | 15.887 | 19.421 |

| RECORD TYPE | ATOM ID NUMBER | ATOM NAME | RESIDUE NAME | CHAIN NAME | RESIDUE ID NUMBER | COORDINATES (x, y, z) | | |
|---|---|---|---|---|---|---|---|---|
| ATOM | 1 | N | ASP | A | 1 | 29.242 | 26.159 | 5.769 |
| ATOM | 2 | CA | ASP | A | 1 | 29.854 | 26.753 | 6.983 |
| ATOM | 3 | C | ASP | A | 1 | 29.732 | 25.793 | 8.161 |
| ATOM | 4 | O | ASP | A | 1 | 29.058 | 24.776 | 8.028 |
| ATOM | 5 | CB | ASP | A | 1 | 29.216 | 28.119 | 7.303 |
| ATOM | 6 | CG | ASP | A | 1 | 29.176 | 29.038 | 6.078 |
| ... | | | | | | | | |
| ATOM | 1602 | 1HZ | LYS | A | 107 | 6.100 | 31.520 | 37.966 |
| ATOM | 1603 | 2HZ | LYS | A | 107 | 5.658 | 29.998 | 37.422 |
| ATOM | 1604 | 3HZ | LYS | A | 107 | 6.576 | 31.051 | 36.542 |
| ATOM | 1605 | N | ASP | B | 1 | 40.617 | 54.935 | 25.812 |
| ATOM | 1606 | CA | ASP | B | 1 | 39.490 | 54.006 | 26.084 |
| ATOM | 1607 | C | ASP | B | 1 | 38.386 | 54.250 | 25.067 |
| ATOM | 1608 | O | ASP | B | 1 | 38.198 | 55.396 | 24.676 |
| ATOM | 1609 | CB | ASP | B | 1 | 38.977 | 54.164 | 27.521 |
| ATOM | 1610 | CG | ASP | B | 1 | 40.098 | 53.796 | 28.488 |
| ... | | | | | | | | |
| ATOM | 3349 | 1HB | ALA | B | 114 | 7.725 | 53.127 | 1.211 |
| ATOM | 3350 | 2HB | ALA | B | 114 | 9.364 | 53.352 | 1.878 |
| ATOM | 3351 | 3HB | ALA | B | 114 | 8.145 | 54.630 | 1.995 |

502

| RECORD TYPE | ATOM ID NUMBER | ATOM NAME | RESIDUE NAME | CHAIN NAME | RESIDUE ID NUMBER | COORDINATES (x, y, z) | | |
|---|---|---|---|---|---|---|---|---|
| ATOM | 3352 | N | LYS | C | 1 | 59.677 | 27.152 | 30.431 |
| ATOM | 3353 | CA | LYS | C | 1 | 59.757 | 25.688 | 30.195 |
| ATOM | 3354 | C | LYS | C | 1 | 60.312 | 25.387 | 28.793 |
| ATOM | 3355 | O | LYS | C | 1 | 60.106 | 26.192 | 27.892 |
| ATOM | 3356 | CB | LYS | C | 1 | 58.361 | 25.064 | 30.411 |
| ATOM | 3357 | CG | LYS | C | 1 | 58.271 | 23.593 | 29.978 |
| ... | | | | | | | | |
| ATOM | 5310 | 1HD2 | LEU | C | 129 | 50.507 | 14.949 | 18.503 |
| ATOM | 5311 | 2HD2 | LEU | C | 129 | 50.145 | 14.519 | 20.177 |
| ATOM | 5312 | 3HD2 | LEU | C | 129 | 49.302 | 15.887 | 19.421 |

FIG.7A

| COORDINATES (x, y, z) | | | ELECTROSTATIC POTENTIAL | NEAREST ATOM |
|---|---|---|---|---|
| 5.717 | 28.98 | 36.679 | 15.123 | ... |
| 6.508 | 28.016 | 36.675 | 1.939 | ... |
| 5.467 | 28.978 | 36.819 | 17.024 | ... |
| 6.618 | 28.098 | 36.46 | 2.250 | ... |
| 5.857 | 29.084 | 36.405 | 12.745 | ... |
| 6.641 | 28.408 | 36.301 | 2.881 | ... |
| ... | | | | |
| 12.456 | 50.666 | 21.096 | 2.245 | ... |
| 12.456 | 49.594 | 20.167 | 2.456 | ... |
| 12.456 | 50.118 | 20.243 | 2.683 | ... |
| 12.456 | 50.517 | 20.589 | 2.076 | ... |
| 12.123 | 50.249 | 21.096 | 1.830 | ... |
| 12.123 | 49.988 | 20.645 | 1.892 | ... |

FIG.7B

| COORDINATES (x, y, z) | | | ELECTROSTATIC POTENTIAL | NEAREST ATOM |
|---|---|---|---|---|
| 38.255 | 33.487 | 10.162 | 16.009 | ... |
| 38.45 | 33.202 | 9.705 | 14.828 | ... |
| 38.34 | 32.247 | 10.171 | 22.630 | ... |
| 38.475 | 34.071 | 9.155 | 10.677 | ... |
| 38.28 | 34.37 | 9.604 | 10.368 | ... |
| 38.557 | 34.381 | 8.681 | 1.255 | ... |
| ... | | | | |
| 50.915 | 3.046 | 22.477 | 3.336 | ... |
| 50.582 | 3.172 | 23.857 | 2.690 | ... |
| 50.582 | 2.692 | 23.637 | 2.654 | ... |
| 50.582 | 2.406 | 23.192 | 2.664 | ... |
| 50.582 | 2.406 | 22.664 | 2.971 | ... |
| 50.582 | 2.692 | 22.219 | 3.006 | ... |

FIG.8

| No. | COORDINATES (x, y, z) | | | ELECTROSTATIC POTENTIAL | SHORTEST DISTANCE [Å] | NEAREST ATOM |
|---|---|---|---|---|---|---|
| 1 | 38.255 | 33.487 | 10.162 | 16.009 | 1.271 | ... |
| 2 | 38.450 | 33.202 | 9.705 | 14.828 | 0.993 | ... |
| 3 | 38.340 | 32.247 | 10.171 | 22.630 | 1.372 | ... |
| 4 | 38.475 | 34.071 | 9.155 | 10.677 | 1.027 | ... |
| ... | | | | | | |
| 300 | 40.525 | 28.749 | 18.909 | 81.380 | 0.000 | ... |
| ... | | | | | | |
| 22851 | 50.582 | 2.406 | 23.192 | 2.664 | 20.642 | ... |
| 22852 | 50.582 | 2.406 | 22.664 | 2.971 | 20.495 | ... |
| 22853 | 50.582 | 2.692 | 22.219 | 3.006 | 20.168 | ... |

FIG.9

| No. | COORDINATES (x, y, z) | | | ELECTROSTATIC POTENTIAL | SHORTEST DISTANCE ≤1.2 [Å] | NEAREST ATOM |
|---|---|---|---|---|---|---|
| 2 | 38.450 | 33.202 | 9.705 | 14.828 | 0.993 | ... |
| 4 | 38.475 | 34.071 | 9.155 | 10.677 | 1.027 | ... |
| ... | | | | | | |
| 300 | 40.525 | 28.749 | 18.909 | 81.380 | 0.000 | ... |
| ... | | | | | | |

FIG.10

| CANDIDATE NUMBER | ELECTROSTATIC POTENTIAL | NEAREST RESIDUE |
|---|---|---|
| 1 | 81.38 | Lys96C |
| 2 | 81.04 | Lys97C |
| 3 | 80.87 | Asp101C |
| ⋮ | ⋮ | ⋮ |

● : REFERENCE POINT
→ : SURFACE NORMAL OF POLYGON

● : REFERENCE POINT
→ : SURFACE NORMAL OF REFERENCE
    POINT VERTEX
--▸ : NORMAL VECTOR OF REFERENCE
    POINT VERTEX

| RECORD TYPE | ATOM ID NUMBER | ATOM NAME | RESIDUE NAME | CHAIN NAME | RESIDUE ID NUMBER | COORDINATES (x, y, z) | | |
|---|---|---|---|---|---|---|---|---|
| ATOM | 1 | N | ASP | A | 1 | 29.634 | 27.057 | 5.364 |
| ATOM | 2 | CA | ASP | A | 1 | 30.639 | 27.33 | 6.419 |
| ATOM | 3 | C | ASP | A | 1 | 30.581 | 26.208 | 7.458 |
| ATOM | 4 | O | ASP | A | 1 | 29.961 | 25.181 | 7.185 |
| ATOM | 5 | CB | ASP | A | 1 | 30.454 | 28.747 | 7.016 |
| ATOM | 6 | CG | ASP | A | 1 | 29.055 | 29.014 | 7.594 |
| ... | | | | | | | | |
| ATOM | 1602 | 1HZ | LYS | A | 107 | 10.856 | 24.195 | 31.969 |
| ATOM | 1603 | 2HZ | LYS | A | 107 | 11.946 | 24.154 | 33.149 |
| ATOM | 1604 | 3HZ | LYS | A | 107 | 10.758 | 22.989 | 33.113 |
| ATOM | 1605 | N | ASP | B | 1 | 41.367 | 52.828 | 28.112 |
| ATOM | 1606 | CA | ASP | B | 1 | 40.260 | 51.941 | 28.558 |
| ATOM | 1607 | C | ASP | B | 1 | 38.991 | 52.328 | 27.81 |
| ATOM | 1608 | O | ASP | B | 1 | 38.721 | 53.520 | 27.692 |
| ATOM | 1609 | CB | ASP | B | 1 | 40.078 | 52.021 | 30.079 |
| ATOM | 1610 | CG | ASP | B | 1 | 41.376 | 51.589 | 30.757 |
| ... | | | | | | | | |
| ATOM | 3349 | 1HB | ALA | B | 114 | 9.626 | 55.330 | 4.296 |
| ATOM | 3350 | 2HB | ALA | B | 114 | 10.51 | 56.810 | 4.31 |
| ATOM | 3351 | 3HB | ALA | B | 114 | 11.405 | 55.289 | 4.145 |
| ATOM | 3352 | N | LYS | C | 1 | 60.03 | 24.917 | 29.094 |
| ATOM | 3353 | CA | LYS | C | 1 | 60.885 | 23.699 | 28.964 |
| ATOM | 3354 | C | LYS | C | 1 | 61.566 | 23.653 | 27.584 |
| ATOM | 3355 | O | LYS | C | 1 | 61.397 | 24.606 | 26.827 |
| ATOM | 3356 | CB | LYS | C | 1 | 60.074 | 22.415 | 29.273 |
| ATOM | 3357 | CG | LYS | C | 1 | 59.001 | 22.040 | 28.227 |
| ... | | | | | | | | |
| ATOM | 5310 | 1HD2 | LEU | C | 129 | 50.414 | 13.681 | 15.073 |
| ATOM | 5311 | 2HD2 | LEU | C | 129 | 50.778 | 12.753 | 16.537 |
| ATOM | 5312 | 3HD2 | LEU | C | 129 | 49.426 | 12.271 | 15.491 |

FIG.23A

| COORDINATES (x, y, z) | | | ELECTROSTATIC POTENTIAL | NEAREST ATOM |
|---|---|---|---|---|
| 38.255 | 33.487 | 10.162 | 16 | ... |
| 38.45 | 33.202 | 9.705 | 14.82 | ... |
| 38.34 | 32.247 | 10.171 | 22.63 | ... |
| ... | | | | |
| 45.556 | 40.603 | 10.986 | -9.98 | ... |
| ... | | | | |
| 47.045 | 49.122 | 13.062 | 43.97 | ... |
| 43.35 | 31.204 | 29.002 | 1.42 | ... |
| 43.35 | 30.684 | 29.002 | 1.54 | ... |

FIG.23B

| COORDINATES (x, y, z) | | | ELECTROSTATIC POTENTIAL |
|---|---|---|---|
| 45.556 | 40.603 | 10.986 | -9.98 |

FIG.24A

| COORDINATES (x, y, z) | | | ELECTROSTATIC POTENTIAL | NEAREST ATOM |
|---|---|---|---|---|
| 38.936 | 33.747 | 12.108 | 43.13 | ... |
| 39.399 | 32.713 | 12.348 | 54.01 | ... |
| 38.954 | 33.836 | 12.495 | 46.11 | ... |
| ... | | | | |
| 42.306 | 24.004 | 16.785 | -9.99 | ... |
| ... | | | | |
| 49.559 | 52.388 | 17.137 | 3.34 | ... |
| 49.559 | 51.947 | 16.222 | 4.86 | ... |
| 49.559 | 52.272 | 16.629 | 2.78 | ... |

FIG.24B

| COORDINATES (x, y, z) | | | ELECTROSTATIC POTENTIAL |
|---|---|---|---|
| 42.306 | 24.004 | 16.785 | -9.99 |

FIG.25

```
REFERENCE_A|ID|CHAIN|SEQUENCE      KVFGRCELAAAMKRHGLDNYRGYSLGNWVCAAKFESNFNTQATNRNTDGS
COMPARISON_A|ID|CHAIN|SEQUENCE     KVFGRCELAAAMKRHGLDNYRGYSLGNWVCAAKFESNFNTQATNRNTDGS
                                   **************************************************

OMITTED

REFERENCE_A|ID|CHAIN|SEQUENCE      DGNGMNAWVAWRNRCKGTDVQAWIRGCRL
COMPARISON_A|ID|CHAIN|SEQUENCE     DGNGMNAWVAWRNRCKGTDVQAWIRGCRL
                                   *****************************

REFERENCE_B|ID|CHAIN|SEQUENCE      DVQLQESGPSLVKPSQTLSLTCSVTGDSITSDYWSWIRKFPGNRLEYMGY
COMPARISON_B|ID|CHAIN|SEQUENCE     DVQLQESGPSLVKPSQTLSLTCSVTGDSITSDYWSWIRKFPGNRLEYMGY
                                   **************************************************

OMITTED

REFERENCE_B|ID|CHAIN|SEQUENCE      DYWGQGTLVTVSAA
COMPARISON_B|ID|CHAIN|SEQUENCE     DYWGQGTLVTVSAA
                                   **************
```

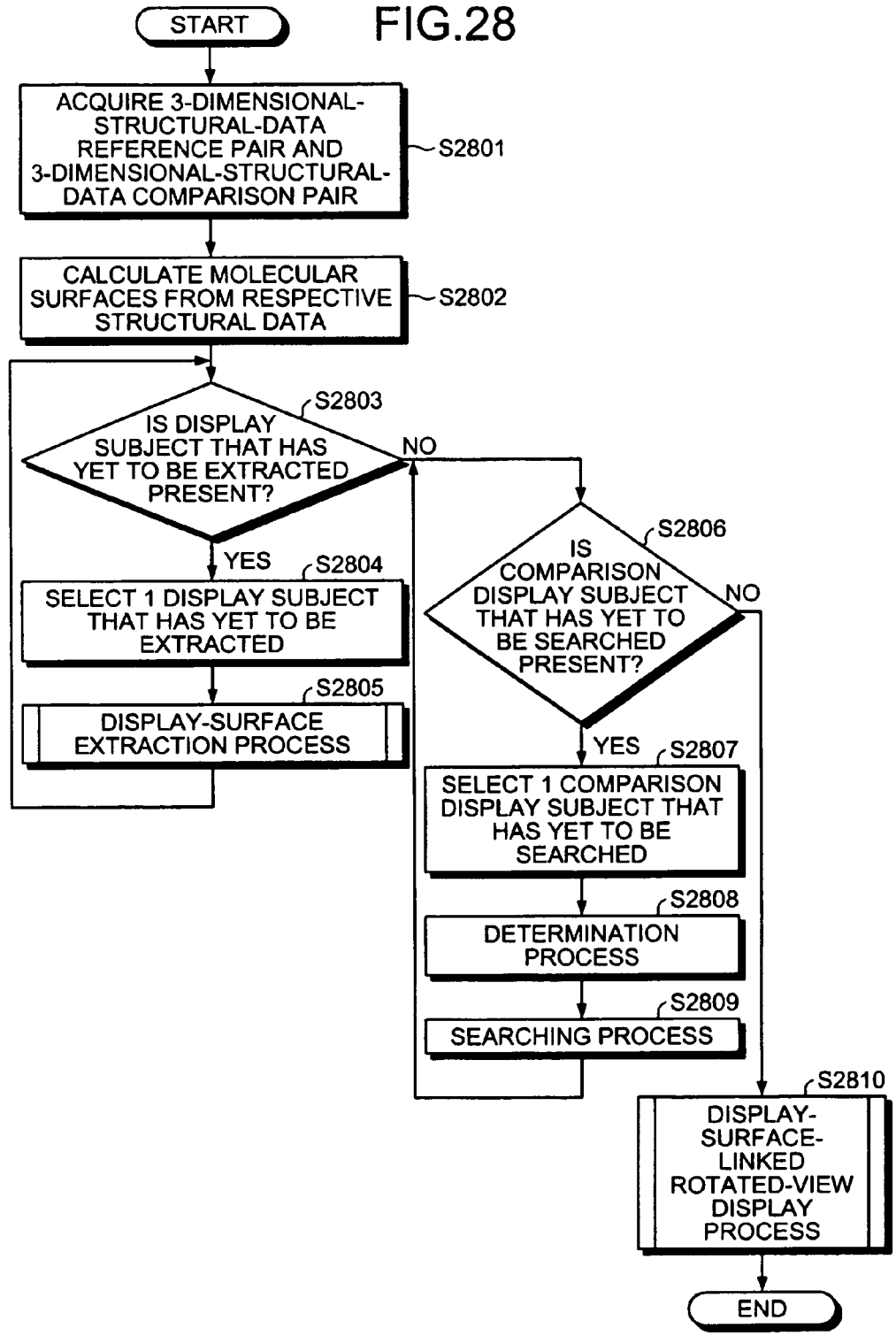

FIG.33

```
GENERATION PROCESS OF NORMAL VECTOR         ~S3202
OF REFERENCE POINT
                    ↓
DETECT AND REGARD AS REFERENCE POINT
AREA, POINT ON DISPLAY SURFACE HAVING
ELECTROSTATIC POTENTIAL WITH SAME          ~S3301
REFERENCE NUMBER AS THAT WITHIN FIRST
GIVEN DISTANCE FROM NEAREST ATOM TO
REFERENCE POINT
                    ↓
WITHIN REFERENCE POINT AREA, DETECT
INNER BORDER AREA THAT IS WITHIN SECOND    ~S3302
GIVEN DISTANCE FROM NEAREST ATOM
                    ↓
SET OUTER BORDER OF REFERENCE POINT
AREA, EXCLUDING INNER BORDER AREA FROM     ~S3303
REFERENCE POINT AREA
                    ↓
CALCULATE CENTER OF MASS OF OUTER          ~S3304
BORDER PORTION OF REFERENCE POINT AREA
                    ↓
SET NORMAL VECTOR THAT IS FROM
REFERENCE POINT AND PASSES THROUGH         ~S3305
CENTER OF MASS
                    ↓
          TO S1603 (S2905)
```

FIG.34

| COORDINATES (x, y, z) | | |
|---|---|---|
| 43.669 | 30.481 | 20.728 |
| 43.841 | 29.349 | 21.594 |
| 43.563 | 28.705 | 21.508 |
| 43.582 | 28.344 | 21.375 |
| 43.745 | 27.966 | 21.25 |
| 43.278 | 26.479 | 20.098 |
| 44.452 | 29.966 | 21.776 |
| 44.34 | 30.737 | 21.115 |
| 44.037 | 30.805 | 20.954 |
| 44.122 | 29.67 | 21.613 |
| ... | | |

FIG.35

| COORDINATES (x, y, z) | | |
|---|---|---|
| 43.669 | 30.481 | 20.728 |
| 43.841 | 29.349 | 21.594 |
| 43.563 | 28.705 | 21.508 |
| 43.582 | 28.344 | 21.375 |
| 43.745 | 27.966 | 21.25 |
| 44.452 | 29.966 | 21.776 |
| 44.34 | 30.737 | 21.115 |
| 44.037 | 30.805 | 20.954 |
| 44.122 | 29.67 | 21.613 |
| 43.778 | 30.572 | 20.826 |
| ... | | |

FIG.36

| COORDINATES (x, y, z) | | |
|---|---|---|
| 43.278 | 26.479 | 20.098 |
| 44.107 | 25.98 | 21.897 |
| 43.97 | 25.979 | 21.538 |
| 43.353 | 26.346 | 20.24 |
| 43.954 | 25.972 | 21.424 |
| 43.876 | 25.853 | 21.432 |
| 47.051 | 27.962 | 22.424 |
| 43.119 | 30.46 | 20.439 |
| 42.31 | 29.936 | 20.492 |
| 42.191 | 29.662 | 20.456 |
| ... | | |

FIG.37

| COORDINATES (x, y, z) | | |
|---|---|---|
| 44.1 | 27.4 | 21.0 |

US 8,427,470 B2

COMPUTER PRODUCT, INFORMATION DISPLAY APPARATUS, AND INFORMATION DISPLAY METHOD

CROSS REFERENCE TO RELATED APPLICATIONS

This is a continuation application of International Application PCT/JP2010/054891 filed on Mar. 19, 2010 which claims priority from International Application PCT/JP2009/056301 filed on Mar. 27, 2009, the contents of which are incorporated herein by reference.

FIELD

The embodiments discussed herein are related to information display.

BACKGROUND

Conventionally, in the development of pharmaceuticals, the determination of binding sites between constituent proteins of protein complexes is an important matter. For example, if the protein complex causing the pathological condition is known, a pharmaceutical candidate that inhibits the formation of the complex is designed based on the shape of a site ("binding site") strongly related to the binding of constituent proteins.

In general, a protein complex is thought be formed by the binding of a constituent protein to another constituent protein by a weak noncovalent interaction at work between constituent proteins in close proximity. A binding site is a constituent protein site related to such an interaction. Therefore, geometric compliments (interlocking shapes) on molecular surfaces of adjacent constituent proteins, electrostatic compliments (positive and negative electrostatic potential occurring between adjacent surfaces), and the like are often searched for as clues.

A 3-D viewer that displays a 3-dimensional configuration of protein on the display of a computing device is known as technology that helps determine binding sites. Based on 3-dimensional structural data (typically, a file storing the types of atoms forming a protein and respective positions on a 3-dimensional coordinate system) of protein and obtained through structural analysis by X-ray, the 3-D viewer creates a figure depicting the 3-dimensional configuration of a protein as viewed from a given direction and displays the figure on the display of the computing device.

Various types of models for expressing the 3-dimensional configuration of a protein are known. For example, there is a model that expresses the shape of protein by the molecular surface obtained from 3-dimensional structural data and expresses the electrostatic potential at points on the molecular surface, by color (e.g., expresses positive electrostatic charge in blue and negative electrostatic charge in red).

Further, for an electrostatic-surface of a functional site (eF-site) that provides the shape and physical properties of a functional site of protein as a database, a tool called a PDBj Viewer that includes a function of displaying a 3-dimensional structure of protein by this type of model has been proposed (see, for example, Kinoshita, K., et al, "eF-site and PDBj-Viewer: database and viewer for protein functional sites", Bioinformatics Vol. 20, No. 8, 2004, pp. 1329-1330). Technology has been disclosed that displays images using pixels as structural elements as well as technology that regards recessed surfaces of macromolecules such as proteins and nucleic acids as potential binding sites and uses the distance at which the binding sites and small molecule ligands can bind, to display ligand-binding pockets of the macromolecules (see for example, Japanese Laid-Open Patent Publication Nos. 2001-22936 and 2009-58499).

However, with the technologies above, if a complex of proteins is to be displayed 3-dimensionally, a problem arises in that adjacent molecular surfaces of proteins become hidden by surrounding molecular surfaces and cannot be seen.

FIG. 38 is diagram of a 3-dimensional model of a protein complex displayed on a display screen. In FIG. 38, an XY plane formed by an X axis and a Y axis, which is orthogonal to the X axis, corresponds to a display screen D and a Z axis is orthogonal to the XY plane and expresses the depth of the display screen D. A 3-dimensional model of a protein complex 100 is an object that is a copy of a 3-dimensional antibody model 101 and a copy of a 3-dimensional antigen model 102.

A 3-dimensional protein complex model 100 is displayed with reference to a 3-dimensional coordinate system of an X axis, a Y axis, and a Z axis. In FIG. 38, the adjacent molecular surfaces of the 3-dimensional antibody model 101 and the 3-dimensional antigen model 102 are hidden by surrounding the molecular surfaces and cannot be seen.

FIGS. 39A and 39B depict the 3-dimensional protein complex model 100 in a rotated state consequent to a user operation. In FIG. 39A, the 3-dimensional antibody model 101 and the 3-dimensional antigen model 102 are displayed separately on display screens D1 and D2. FIG. 39A depicts the 3-dimensional antibody model 101 and the 3-dimensional antigen model 102 before rotation and FIG. 39B depicts the states thereof after rotation. Consequent to a user operation, the 3-dimensional antibody model 101 rotates about an axis Ay1 that is parallel to the Y axis and the 3-dimensional antigen model 102 rotates about an axis Ay2 that is parallel to the Y axis.

As depicted in FIGS. 39A and 39B, so that electrical characteristics of the molecular surfaces can be visually discerned, the respective constituent proteins have to be displayed separately such as on the display screens D1 and D2. Further, as depicted in FIG. 39B, the user has to designate the appropriate direction of rotation when the constituent proteins are to be rotated in a direction to enable the electrical characteristics of the adjacent molecular surfaces to be viewed.

SUMMARY

According to an aspect of an embodiment, a computer-readable, non-transitory medium storing therein an information display program causes a computer to execute a process. The process includes acquiring a 3-dimensional structural data pair that includes 3-dimensional structural data for a display subject and 3-dimensional structural data of a comparison subject that is compared to the display subject; extracting as a display surface of the display subject and from among display subject surfaces identified by the display subject acquired at the acquiring, a surface that is within a given distance from a comparison subject surface identified by the comparison subject; selecting a reference point from among vertices forming the extracted display surface of the display subject, the selecting being based on the amount of characteristics of the vertices; generating the normal of the selected reference point; setting a rotation axis about which the generated normal of the reference point is rotated to point in a counter viewing direction; calculating based on the normal of the reference point and the normal of the display surface and according to the uneven shape of the display surface, an angle of rotation by which the normal of the reference point is rotated about the rotation axis to point in the counter viewing direction; converting coordinates of the vertices into coordinates of the vertices in a state where the normal of the reference point has been rotated by the calculated angle of rotation and points in the counter viewing direction; and drawing on a display screen and based on the amount of characteristics, the display surface of the display subject, from a viewing direction subsequent to conversion at the converting.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 3 is a block diagram of a functional configuration of the information display apparatus according to the first embodiment.

FIG. 4 is a diagram of 3-dimensional structural data of a protein complex.

FIG. 5A is a diagram of the 3-dimensional structural data of an antibody (comparison subject).

FIG. 7A is a diagram of molecular-surface structural data that represents a molecular surface of the antibody that is the comparison subject.

FIG. 7B is a diagram of molecular-surface structural data that represents a molecular surface of the antigen that is the display subject.

FIG. 8 is a diagram of the shortest distance data saved for molecular-surface structural data of the display subject (antigen).

FIG. 9 is a diagram of display surface structural data.

FIG. 10 is a table of the nearest residues sorted in descending order of electrostatic potential.

FIG. 22 is a diagram of 3-dimensional structural data that is for a comparison protein complex and from which a 3-dimensional-structural-data comparison pair is derived.

FIG. 23A is a diagram of the molecular-surface structural data that represents the molecular surface S of the antibody that is reference display subject.

FIG. 23B is a diagram of reference point data that indicates the reference point of a molecular surface of the antibody that is the reference display subject.

FIG. 24A is a diagram of molecular-surface structural data representing a molecular surface of the antibody that is comparison display subject.

FIG. 24B is a diagram of reference point data that indicates the reference point of the molecular surface of the antibody that is the comparison display subject.

FIG. 25 is diagram of an execution example of multiple sequence alignment.

FIG. 28 is a flowchart of the information display process performed by the information display apparatus according to the third embodiment.

FIG. 33 is a flowchart of a normal vector generation process (step S3202) depicted in FIG. 32.

FIG. 34 depicts an example of coordinate data of the reference point area set at step S3301.

FIG. 35 depicts an example of coordinate data of an inner border area set at step S3302 for the reference point area.

FIG. 36 depicts an example of coordinate data of an outer border set at step S3303 for the reference point area.

FIG. 37 is an example of coordinate data of the center of mass W calculated using the coordinate data of the outer border set at step S3303 for the reference point area.

DESCRIPTION OF EMBODIMENTS

Preferred embodiments of the present invention will be explained with reference to the accompanying drawings. In the embodiments, an object is displayed on a display screen D in which a plane formed by the X and the Y axis is regarded as an XY plane, and an axis orthogonal to the XY plane is regarded as a Z axis in a 3-dimensional coordinate system. Along the Z axis, in a direction away from the origin is the viewing direction from the viewing coordinate system and the opposite direction is a counter viewing direction. In the present embodiments, description will be given where the object is a 3-dimensional model of protein.

Figure 1A:
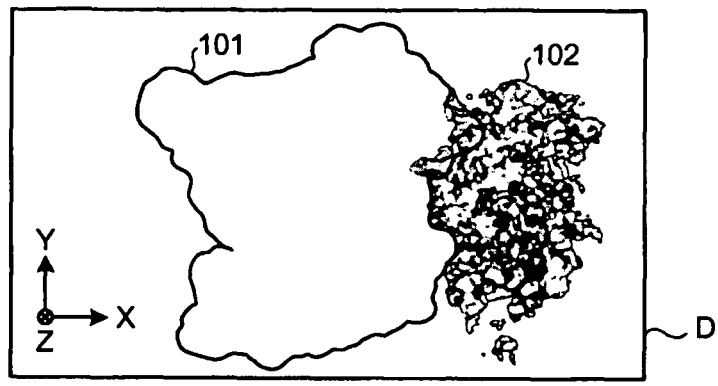
FIGS. 1A, 1B, 1C, and 1D depict an overview of the present embodiment.

FIGS. 1A to 1D depict an overview of the present embodiment. FIG. 1A depicts the state and the same contents as FIG. 30. Here, a 3-dimensional antigen model 102 is regarded as a display subject and a 3-dimensional antibody model 101 is regarded as a comparison subject of the 3-dimensional antigen model 102. The 3-dimensional antigen model 102 is colored according to an electrical characteristic, electrostatic potential. On the other hand, although the antibody also has electrostatic potential, since the 3-dimensional antibody model 101 is not the display subject, the 3-dimensional antibody model 101 is not colored according to electrostatic potential. Therefore, in FIG. 1, the 3-dimensional antibody model 101 is depicted as only a silhouette.

Figure 1B:
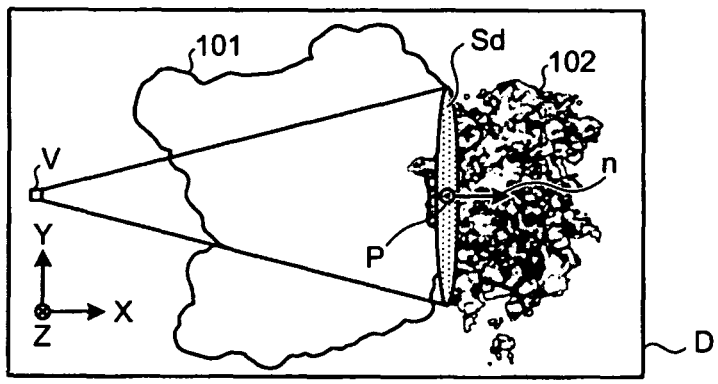

FIG. 1B depicts a display surface Sd cutout. The display surface Sd is a portion of the molecular surface of the display subject and is within a distance enabling binding with the comparison subject. Since the molecular surface is typically uneven, the display surface Sd is also uneven, however, in FIG. 1B, the unevenness is not depicted for simplicity. When modeling is performed, a modeling coordinate system that specifies reference coordinates of the molecular surface and the normal thereof is used. Here, a reference point P on a convex aspect and the normal vector n thereof is displayed. Since the normal vector n of the convex aspect faces toward the interior of the molecule, the viewpoint V is in the opposite direction of the normal vector n. On the other hand, at a concave aspect, since the normal vector of the reference point faces toward the exterior of the molecule, the viewpoint V is in the same direction as the normal vector.

Figure 1C:
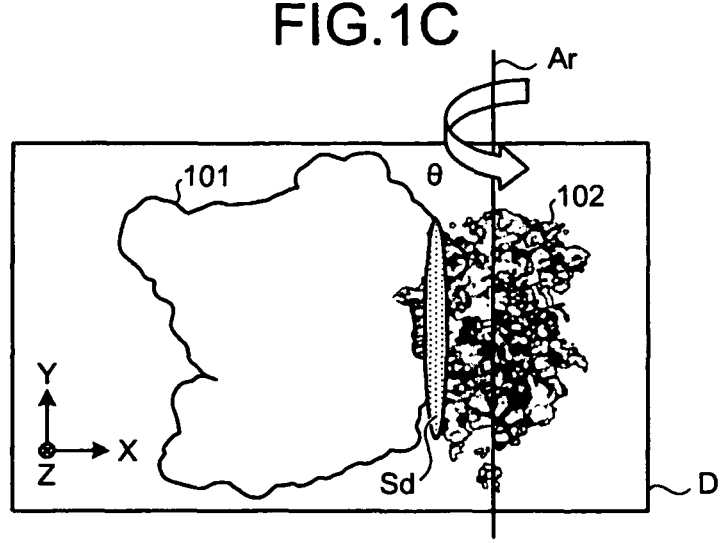

FIG. 1C depicts, in a rotated state, the 3-dimensional antigen model 102, which is the display subject. Here, rotation is about an axis of rotation Ar. In modeling coordinate systems, often the origin is placed at the structural center of mass and the positive direction of the y axis is set as the upward direction of the perpendicular. In the case of the 3-dimensional antigen model 102 displayed toward the right as a protein complex, the origin is placed at the center of mass of the antigen and the antigen is rotated counterclockwise toward the Y axis, as the axis of rotation Ar. The angle of rotation is an angle θ between the display surface before rotation and a reference point display surface. The 2 planes formed by the angle θ are equivalent to the normal vector of the selected reference point and the normal vector of the display surface before rotation. If θ<90 is true, θ is used at a convex aspect and if θ>90 is true, at a concave aspect, since the normal is in the opposite direction, an angle of θ-180 degrees is used as the angle of rotation. If the 3-dimensional antibody model 101 is the display subject, the antibody is rotated clockwise toward the Y axis.

Figure 1D:
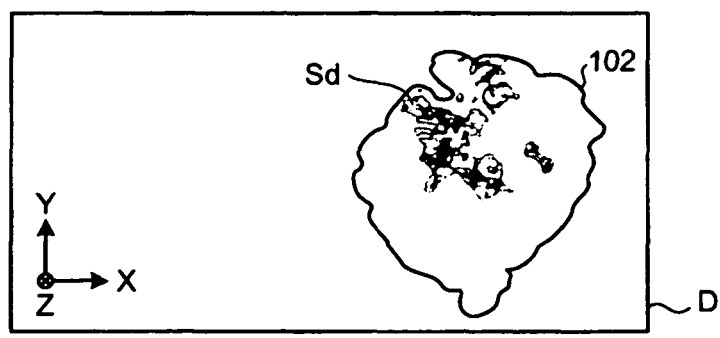

FIG. 1D depicts the display state after the rotation depicted in FIG. 1C. In FIG. 1D, only the display surface Sd is displayed in color and molecular surfaces other than the display surface Sd are displayed in color (although the other molecular surfaces may be displayed in color, the coloring is such that the display surface Sd can be identified). Consequently, in the state depicted in FIG. 1A, the display surface Sd of the 3-dimensional antigen model 102 that is within a distance enabling binding with the antibody can be displayed at a position that is easily viewed by the user. Although here the 3-dimensional antigen model 102 has been regarded as the display subject, the same is true of the 3-dimensional antibody model 101 if regarded as the display subject.

Figure 2:
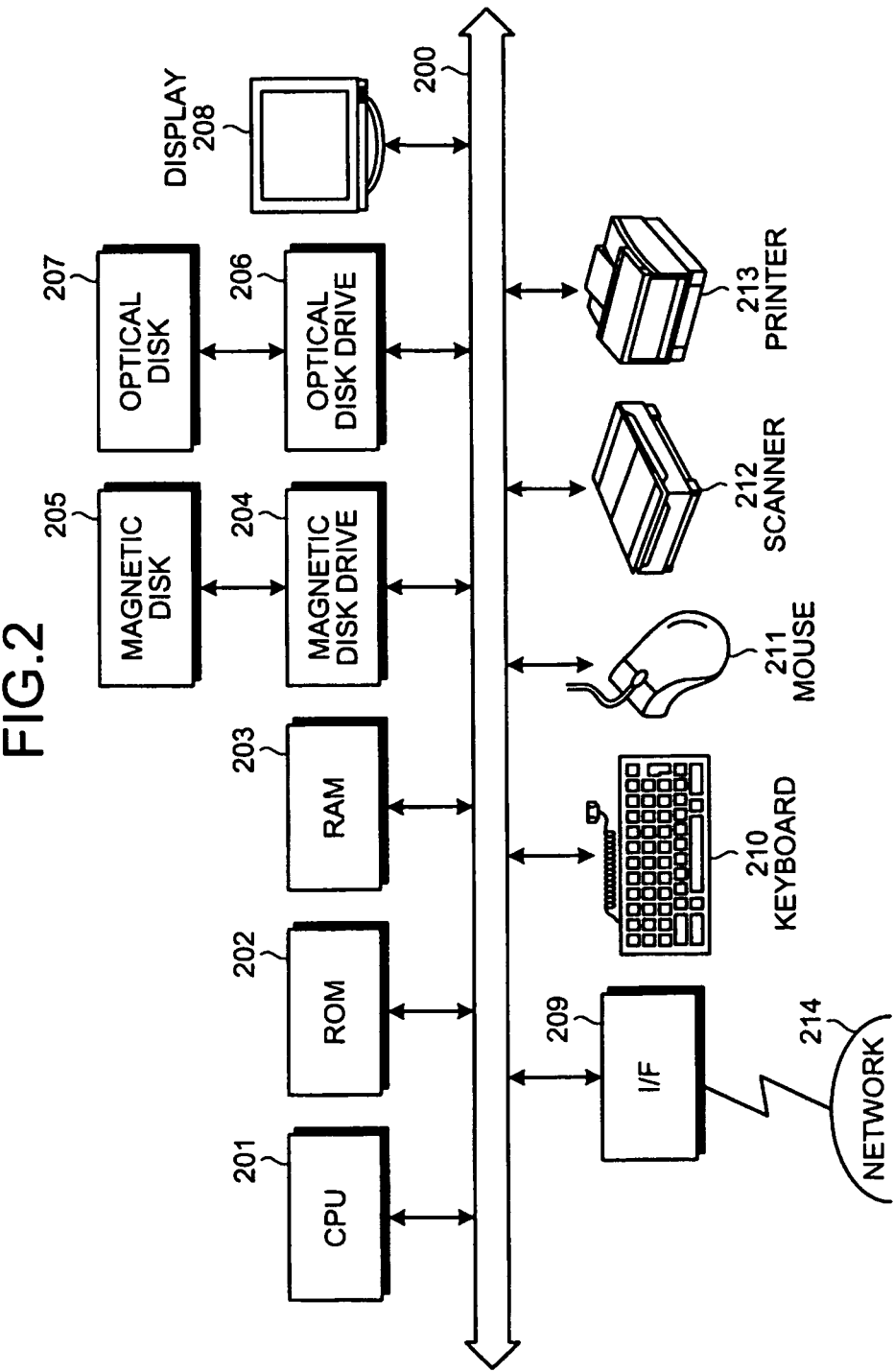
FIG. 2 is a block diagram of a hardware configuration of an information display apparatus according to the embodiments.

FIG. 2 is a block diagram of a hardware configuration of an information display apparatus according to the embodiments (common to the first to the fourth embodiments). As depicted in FIG. 2, the information display apparatus includes a central processing unit (CPU) 201, a read-only memory (ROM) 202, a random access memory (RAM) 203, a magnetic disk drive 204, a magnetic disk 205, an optical disk drive 206, an optical disk 207, a display 208, an interface (I/F) 209, a keyboard 210, a mouse 211, a scanner 212, and a printer 213, respectively connected by a bus 200.

The CPU 201 governs overall control of the information display apparatus. The ROM 202 stores therein programs such as a boot program. The RAM 203 is used as a work area of the CPU 201. The magnetic disk drive 204, under the control of the CPU 201, controls the reading and writing of data with respect to the magnetic disk 205. The magnetic disk 205 stores therein data written under control of the magnetic disk drive 204.

The optical disk drive 206, under the control of the CPU 201, controls the reading and writing of data with respect to the optical disk 207. The optical disk 207 stores therein data written under control of the optical disk drive 206, the data being read by a computer.

The display 208 displays, for example, data such as text, images, functional information, etc., in addition to a cursor, icons, and/or tool boxes. A cathode ray tube (CRT), a thin-film-transistor (TFT) liquid crystal display, a plasma display, etc., may be employed as the display 208.

The I/F 209 is connected to a network 214 such as a local area network (LAN), a wide area network (WAN), and the Internet through a communication line and is connected to other apparatuses through the network 214. The I/F 209 administers an internal interface with the network 214 and controls the input/output of data from/to external apparatuses. For example, a modem or a LAN adaptor may be employed as the I/F 209.

The keyboard 210 includes, for example, keys for inputting letters, numerals, and various instructions and performs the input of data. Alternatively, a touch-panel-type input pad or numeric keypad, etc. may be adopted. The mouse 211 is used to move the cursor, select a region, or move and change the size of windows. A track ball or a joy stick may be adopted provided each respectively has a function similar to a pointing device.

The scanner 212 optically reads an image and takes in the image data into the design support apparatus. The scanner 212 may have an optical character reader (OCR) function as well. The printer 213 prints image data and text data. The printer 213 may be, for example, a laser printer or an ink jet printer.

Hereinafter, the first to the fourth embodiments will be described. In the first embodiment, the basic configuration of the technology depicted in FIG. 1 is shown and as for the 2 proteins (an antigen and a antibody) forming a complex, one protein is regarded as a display subject and the other is regarded as a comparison subject. The display surface Sd is cutout from a molecular surface S of the display subject. Subsequently, based on the amount of characteristics that each vertex forming the cutout display surface Sd has, a reference point is selected from the group of vertices. Consequently, since the normal vector of the selected reference point becomes the normal vector n of the display surface Sd, by converting the direction of the normal vector n to the counter viewing direction, the display surface Sd is displayed.

FIG. 3 is a block diagram of a functional configuration of the information display apparatus according to the first embodiment. An information display apparatus 300 includes an acquiring unit 301, an extracting unit 302, a selecting unit 303, a generating unit 304, a setting unit 305, an angle-of-rotation calculating unit 306, a converting unit 307, and a drawing unit 308. These functions (the acquiring unit 301 to the drawing unit 308) forming a control unit, for example, are implemented by executing on the CPU 201, programs stored in a storage device such as the ROM 202, the RAM 203, the magnetic disk 205, and the optical disk 207 depicted FIG. 2, or by the I/F 209.

The acquiring unit 301 has function of acquiring a 3-dimensional structural data pair that is a combination of the 3-dimensional structural data of the display subject and the 3-dimensional structural data of the comparison subject to which the display subject is compared. Here, the 3-dimensional structural data pair is 3-dimensional structural data of the display subject for displaying the display surface Sd and 3-dimensional structural data of the comparison subject that is compared to the display subject.

A 3-dimensional model of the display subject and the comparison subject is generated based on the respective 3-dimensional structural data. In the first embodiment, as a 3-dimensional structural data pair, an example of 3-dimensional structural data related to a protein complex will be described. Among the constituent proteins of the protein complex, one (e.g., an antibody) is regarded as a comparison subject and the other (e.g., an antigen) is regarded as a display subject.

FIG. 4 is a diagram of 3-dimensional structural data of the protein complex. In FIG. 4, the 3-dimensional structural data 400 of the protein complex has a record for each constituent element of the protein complex, each record including a record type field, an atom identification (ID) number field, an atom name field, a residue name field, a chain name field, a residue ID number field, and a coordinate field.

The record type indicates the type of the record representing the constituent element. In this example, the record type indicates "ATOM" since the constituent elements are atoms. Therefore, records in which the record type is "ATOM", are records for constituent elements that are atoms. An atom ID number is an identification number unique to each record. The atom name is the name of the atom specified by the record. The residue name is the name of the amino acid residue specified by the record.

The chain name is the name identifying the peptide chain (a polymer of a continuous chain of amino acids bonded by peptide bonds), which is a fundamental structural unit of protein. For example, in a protein formed by 2 peptide chains, the names of chain A and chain B are given. The residue ID number is an identification number unique to each amino acid residue. The coordinates are positional information for an atom in a 3-dimensional modeling coordinate system in which the origin is a specified position (e.g., the center of mass of the protein complex or the center of mass of any one of the constituent proteins, etc.). If position is expressed in a viewing coordinate system, a known coordinate conversion is performed.

When the 3-dimensional structural data 400 of the protein complex depicted in FIG. 4 is input as input data, the 3-dimensional structural data 400 is separated by the chain name, into the 3-dimensional structural data of the antibody and the 3-dimensional structural data of the antigen, whereby the 3-dimensional structural data pair is acquired. The separation of the antibody and the antigen data is performed according to the chain name in the 3-dimensional structural data 400 of the protein complex. In the 3-dimensional structural data 400 of the protein complex depicted in FIG. 4, chain A and chain B records are separated as antibodies (comparison subject) and chain C records are separated as antigens (display subject).

Figures 5B, 6:
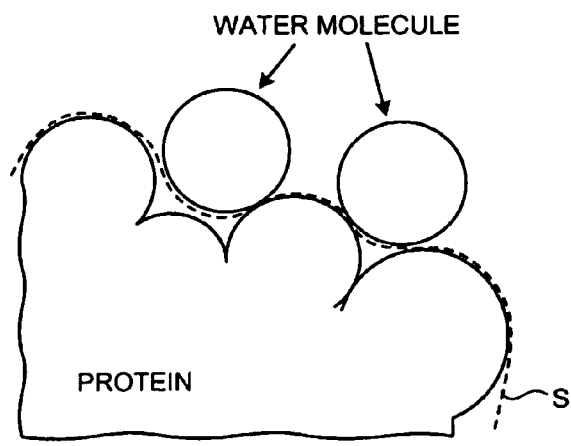
FIG. 5B is a diagram of the 3-dimensional structural data of an antigen (display subject).
FIG. 6 is a diagram of molecular surface identification.

FIG. 5A is a diagram of the 3-dimensional structural data of an antibody (comparison subject) and FIG. 5B is a diagram of the 3-dimensional structural data of an antigen (display subject). The 3-dimensional structural data of an antibody 501 depicted in FIG. 5A, is the data for chain A and chain B in the 3-dimensional structural data 400 of the protein complex depicted in FIG. 4. The 3-dimensional structural data of an antigen 502 depicted in FIG. 5B, is the data of chain C in the 3-dimensional structural data 400 of the protein complex depicted in FIG. 4.

Here, by separating the 3-dimensional structural data 400 of the protein complex according antibody and antigen, the 3-dimensional structural data pair (501, 502) for the antibody and the antigen is acquired, however, configuration may be such that positional relationship data of preliminarily separated 3-dimensional structural data pairs for the antibodies and the antigens is acquired. Further, configuration is not limited to a protein complex and may be such that positional relationship data of a 3-dimensional structural data pair for 2 arbitrary proteins is acquired.

The extracting unit 302 has a function of acquiring the display surface Sd of the display subject (antigen) as depicted in FIG. 1. For example, among the surfaces of the display subject identified by the display subject acquired by the acquiring unit 301, the extracting unit 302 extracts, as the display surface Sd, a surface that is within a given distance from a surface of the comparison subject, identified by the comparison subject. This function is the function depicted in FIG. 1B and for example, cuts out from the molecular surface of the antigen (display subject) as the display surface Sd of the antigen, a surface that is within a given distance from the molecular surface of the antibody (comparison subject). Here, the molecular surface will be described.

FIG. 6 is a diagram of molecular surface identification. For example, atoms in the protein are assumed to be hard spheres of a Van der Waals radius, where the molecular surface S is defined as an inner contact surface making contact between an external side and water molecules (hard spheres of a conventional diameter of 1.4 [angstrom]). The Van der Waals radius indicates the width of the electron cloud of each atom as the radius of a hard sphere assigned to each atom. In general, the Van der Waals radius is estimated using the bonding length between atoms, obtained by low molecular X-ray crystallographic analysis, using contact distance, etc. Since the molecular surface S can be identified by known calculation methods, description thereof is omitted (for example, the calculation method described in Sanner, M. F., et al, "Reduced surface: an efficient way to compute molecular surfaces", Biopolymers, Vol. 38(3): 305-320 (1996), pp. 1-28 is used). In the first embodiment, the atoms and coordinates specified by the records in the 3-dimensional structural data 501 and 502 depicted in FIGS. 5A and 5B identify coordinates of the vertices of polygons forming the molecular surface S.

FIG. 7A is a diagram of molecular-surface structural data that represents the molecular surface S of the antibody that is the comparison subject. FIG. 7B is a diagram of molecular-surface structural data that represents the molecular surface S of the antigen that is the display subject. In FIGS. 7A and 7B, molecular-surface structural data 701 and 702 have a record for each vertex of a polygon forming the molecular surface S, where each record includes the coordinates of the vertex and the electrostatic potential at the vertex. Coordinate data for the vertices of the polygons forming the molecular surface S in the drawings are the results of calculation by the method described in Sanner, M. F., et al, "Reduced surface: an efficient way to compute molecular surfaces", Biopolymers, Vol. 38(3): 305-320 (1996), pp. 1-28.

The electrostatic potential is an electric characteristic representing the sum of the Coulomb potential between atoms each having partial charge in the protein. The electrostatic potential is calculated by the extracting unit 302. Since calculation methods of electrostatic potential are known, description thereof will be omitted and a calculation method described by, for example, Rocchia, W., et al, "Electrostatic potential calculation for biomolecules-creating a database of pre-calculated values reported on a per residue basis for all PDB protein structures", Genet. Mol. Res., 6(4): 923-936 (2007), pp. 923-936 or Lu, B. Z. et al, "Recent progress in numerical methods for the Poisson-Boltzmann equation in biophysical applications", Commun. in Comput. Phys., Vol. 3(5): 973-1009 (2008), pp. 973-1009 is used. The nearest atom is the ID number of the atom located nearest to the corresponding vertex. By setting the nearest atom as a key, the amino acid residue formed by the atoms can be identified from the records depicted in FIGS. 5A and 5B. In the first embodiment, although calculation of the electrostatic potential on the molecular surface S of the display subject alone is sufficient, in FIG. 7A, the results of calculation concerning the electrostatic potential on the molecular surface S of the comparison subject used in the second embodiment are also depicted.

If the molecular surfaces S of the comparison subject (antibody) and of the display subject (antigen) are specified as the molecular-surface structural data 701 and 702, the extracting unit 302 calculates from the vertex coordinates of the molecular-surface structural data records for the display subject, the shortest distance to the molecular surface S of the comparison subject. For example, the extracting unit 302 selects 1 set of vertex coordinates from the molecular-surface structural data 702 for the display subject, calculates the distance to the vertex coordinates of each of the polygons forming the molecular surface S of the comparison subject, and saves only the shortest distance among the calculated distances. This processing is executed for all of the records in the molecular-surface structural data 702 of the display subject.

FIG. 8 is a diagram of the shortest distance data saved for the molecular-surface structural data 702 of the display subject (antigen). In the shortest distance data 800 depicted in FIG. 8, a shortest distance field is added to the molecular-surface structural data of the display subject (antigen) depicted in FIG. 7B. From the shortest distance data 800, the extracting unit 302 extracts records in which the shortest distance is less than or equal to a given distance enabling binding with the comparison subject (e.g., 1.2 [angstrom]). The portion of the molecular surface S identified by the extracted records is extracted as the display surface Sd.

FIG. 9 is a diagram of display surface structural data. Display surface structural data 900 depicted in FIG. 9 is a collection of records from the shortest distance data 800 depicted in FIG. 8 and in which the shortest distance is less than or equal to a given distance (e.g., 1.2 [angstrom]).

In FIG. 3, the selecting unit 303 has a function of selecting as a reference point, a point having a characteristic of interest. Based on the amounts of characteristics of the vertices of the display surface Sd of the display subject extracted by the extracting unit 302, the selecting unit 303 selects the point from among the vertices. Here, the amount of characteristics of the vertices forming the display surface Sd is characteristic-information given to the vertices like the electrostatic potential above.

Hereinafter, although an example in which a vertex where the absolute value of the electrostatic potential is the greatest is selected as the reference point, configuration may be such that vertices having the highest n absolute values of the electrostatic potential are extracted and displayed on the display screen D and from among the displayed vertices, the user makes a selection. Further, configuration may be such that for selected reference point candidates that have the same residue (e.g., a polar amino acid residue) or atom (e.g., nitrogen, oxygen) that may be associated with noncovalent bond formation nearest the selected reference point candidate, only the candidate having the greatest absolute value is stored and the other candidate(s) is deleted.

FIG. 10 is a table of the nearest residues sorted in descending order of electrostatic potential. In FIG. 10, the electrostatic potential in the display surface structural data 900 depicted in FIG. 9 is sorted in descending order. The selecting unit 303 can refer to the table depicted in FIG. 10 to select the reference point.

The generating unit 304 has function of generating the normal of the reference point selected by the selecting unit 303. For example, the generating unit 304 obtains the normal vector n of a reference point vertex. The generating 304, for example, obtains the surface normal of each polygon having the reference point as a vertex and then, sums and normalizes the surface normals, whereby the normal vector n of the reference point vertex is generated.

Figure 11:
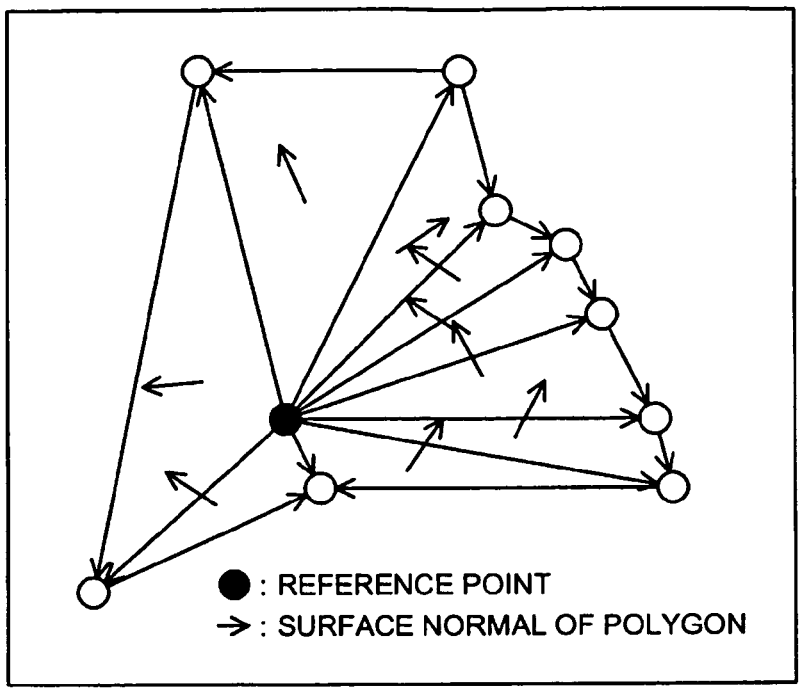
FIG. 11 is a plane view of surface normals of a display surface near a reference point.

FIG. 11 is a plane view of the surface normals of the display surface Sd near the reference point. In FIG. 11, triangular shapes represent polygons forming the display surface Sd and circular shapes represent vertices of the polygons. In particular, the black dot represents the reference point. Arrows on the polygons represent the surface normals of the polygons.

Figure 12:
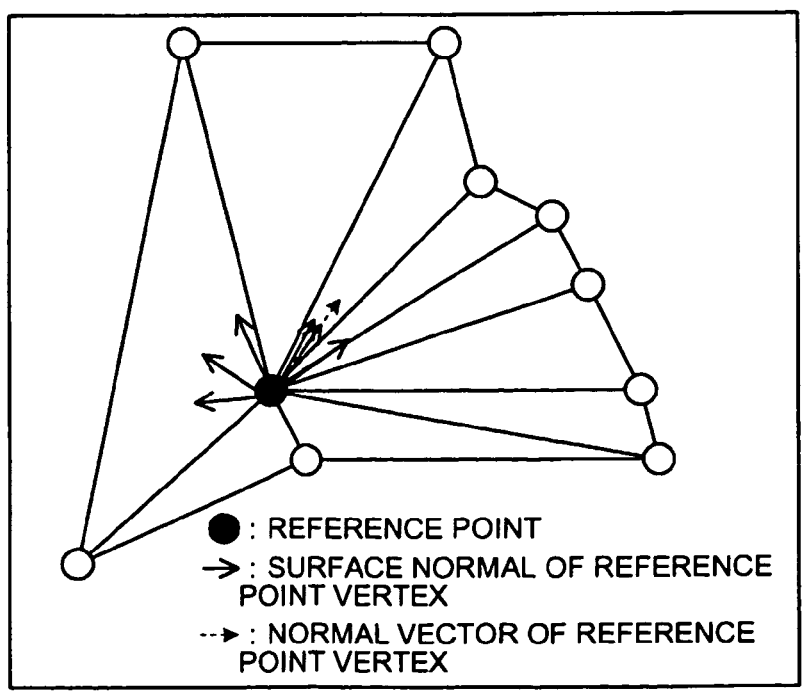
FIG. 12 is a plane view of normal vectors of vertices of the display surface near the reference point.

FIG. 12 is a plane view of normal vectors of vertices of the display surface Sd near the reference point. By summing and normalizing the surface normals depicted in FIG. 11, the normal vector of the reference point vertex can be obtained. In FIG. 12, the dotted-lined arrow represents the normal vector of the reference point vertex.

The setting unit 305 has a function of setting the rotation axis for rotating to the counter viewing direction, the normal of the reference point generated by the generating unit 304. For example, the setting unit 305 sets, as the rotation axis, the Y axis of a modeling coordinate system in which the origin is at the structural center of mass and the positive direction of the Y axis is defined as an upward, vertical direction.

The angle-of-rotation calculating unit 306 has a function of calculating the angle of rotation θ for rotating to the counter viewing direction, the normal vector n of the reference point generated by the generating unit 304. For example, by obtaining the inner product of the normal vector n of the reference point vertex and the normal vector of the display surface before rotation, the angle-of-rotation calculating unit 306 obtains the angle between the normal vector n of the vertex and the normal vector of the display surface before rotation, as the angle of rotation θ.

The converting unit 307 has a function of converting the coordinates of the vertices forming the display surface Sd of the display subject, into coordinates of the vertices in a state where the normal vector n of the reference point has been rotated to the counter viewing direction by the angle of rotation θ calculated by the angle-of-rotation calculating unit 306. For example, the converting unit 307 converts the coordinates of the vertices of the polygons forming the display surface Sd, using a rotation matrix for rotating the normal vector n of the reference point about the rotation axis by the angle of rotation θ. In addition to the vertices of the polygons forming the display surface Sd, this coordinate conversion may be executed with respect to the vertices forming the polygons of the molecular surface S, the coordinates of the atoms nearest to the molecular surface S and from which the molecular surface S is generated, etc.

An example in which OpenGL (http://www.opengl.org/ (searched Mar. 8, 2010)) is used will be given. OpenGL is an application program interface (API) that is used for controlling graphic hardware from a program, in 3-dimensional graphics. The following 4 coordinate conversion processes are implemented on hardware.

1. Determine position in the graphic space "modeling conversion"
2. Correct the space to be a space viewed from a viewpoint "viewing (visual field) conversion"
3. Project the space on a screen in a space inside a computer "transparency conversion"
4. Cut out graphic on screen to display area on display "view port conversion"

Further, in performing animation (repetition) of images, although a coordinate conversion matrix has to be set for each image, this operation can be implemented on the hardware.

The drawing unit 308 has a function of drawing on the display screen D and based on the amount of characteristics, the display surface Sd of the display subject, as viewed from the viewing direction after conversion by the converting unit 307. For example, the drawing unit 308 draws polygons forming the display surface Sd after conversion. The surfaces of the polygons are colored according to the electrostatic potential. Molecular surfaces S other than the display surface Sd need not be colored (or are monochrome, black/white). Further, a silhouette of the display subject may be drawn. At the drawing unit 308, for example, structural data and coloration data for the display surface Sd is transferred to a non-depicted drawing device that writes to video RAM (VRAM), whereby the display surface Sd after rotation processing and the electrostatic potential are displayed on the display screen D.

Further at the drawing unit 308, although the drawing described above related to the vertices forming the display surface Sd is performed, configuration may be such that in place of the display surface Sd, the atoms nearest the vertices forming the display surface Sd are drawn. For example, the nearest atoms can be identified from the nearest atom field in the display surface structural data 900 depicted in FIG. 9. Consequently, since the amino acid residue formed by the nearest atoms can also be identified, the nearest amino acid residue can also be drawn.

Figure 13:
FIG. 13 depicts an example of an image on a display screen after rotation of the view according to the first embodiment.

FIG. 13 depicts an example of an image on the display screen after rotation of the view according to the first embodiment. In FIG. 13, a 3-dimensional model 1302 related to the display surface structural data 900 of the antigen, which is one of the proteins, is depicted in a rotated state by the process according to the first embodiment. The reference point P, which is candidate 1 depicted in FIG. 10, is also displayed.

Figure 14:
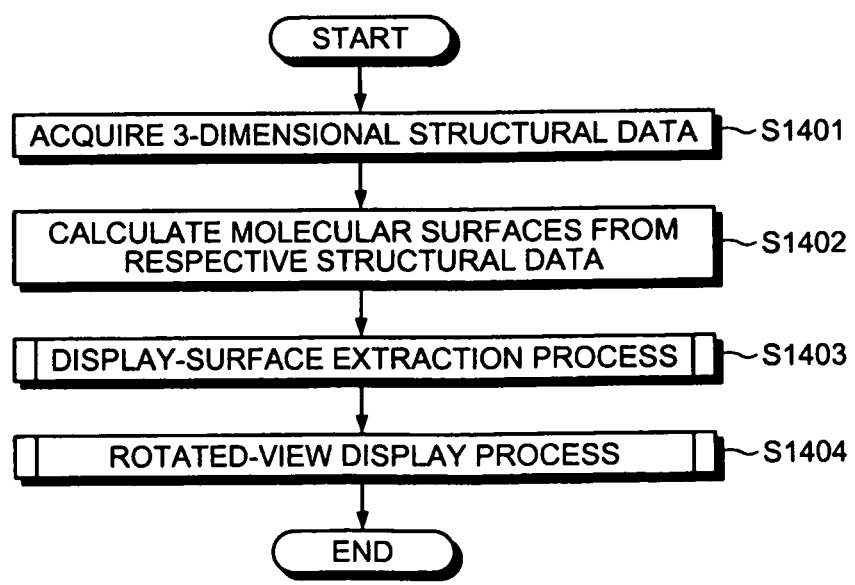
FIG. 14 is a flowchart of an information display process by the information display apparatus according to a first embodiment.

FIG. 14 is a flowchart of an information display process by the information display apparatus according to the first embodiment. The acquiring unit 301 acquires the 3-dimensional structural data 400 of a protein complex, i.e., 3-dimensional structural data pair (step S1401). The information display apparatus separates the acquired 3-dimensional structural data 400 of the protein complex into 3-dimensional structural data of the display subject and 3-dimensional structural data of the comparison subject.

The information display apparatus calculates the molecular surface S concerning the 3-dimensional structural data of the display subject and the 3-dimensional structural data of the comparison subject (step S1402). Upon calculating the molecular surface S, the information display apparatus executes the display-surface extraction process with respect to the molecular surface S of the display subject and the molecular surface S of the comparison subject (step S1403). Consequently, the information display apparatus cuts out the display surface Sd from the molecular surface S of the display subject. Subsequently, the information display apparatus executes a rotated-view display process the cut out display surface Sd (step S1404), enabling the display surface Sd to be displayed from a perspective easily viewed by the user.

Figure 15:
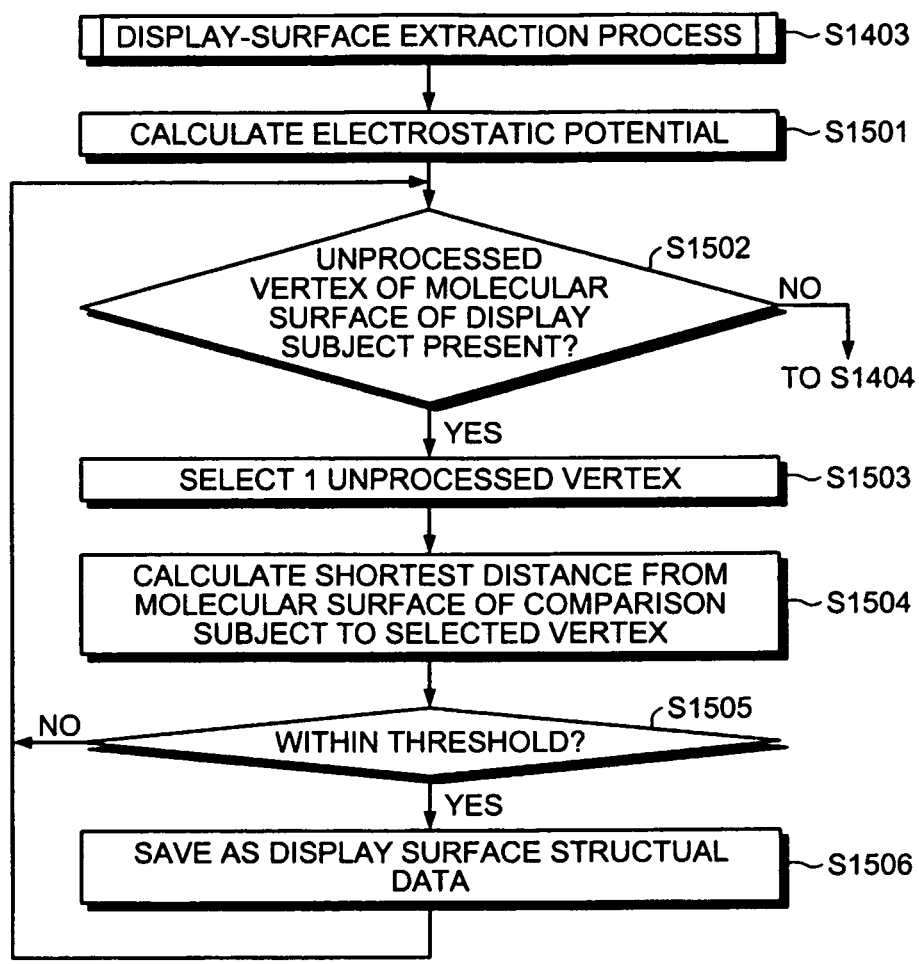
FIG. 15 is a flowchart of a display-surface extraction process (step S1403) depicted in FIG. 14.

FIG. 15 is a flowchart of the display-surface extraction process (step S1403) depicted in FIG. 14. The information display apparatus calculates electrostatic potential of the molecular surface S of the display subject (step S1501) and determines whether an unprocessed vertex is present among the vertices of the polygons forming the molecular surface S of the display subject (step S1502).

If an unprocessed vertex is present (step S1502: YES), the information display apparatus selects one unprocessed vertex (step S1503). The information display apparatus calculates the distance from the vertices of the polygons forming the molecular surface S of the comparison subject, to the selected vertex and regards the shortest distance thereamong as the "shortest distance" (step S1504). The information display apparatus determines whether the shortest distance is with in a threshold (step S1505).

If the shortest distance is within the threshold (step S1505: YES), the selected vertex is stored as display surface structural data (step S1506), and the information display apparatus proceeds to step S1502. On the other hand, if the shortest distance is not within the threshold (step S1505: NO), the information display apparatus returns to step S1502. At step S1502, if no unprocessed vertices are present (step S1502: NO), the information display apparatus transitions to the rotated-view display process (step S1404).

Figure 16:
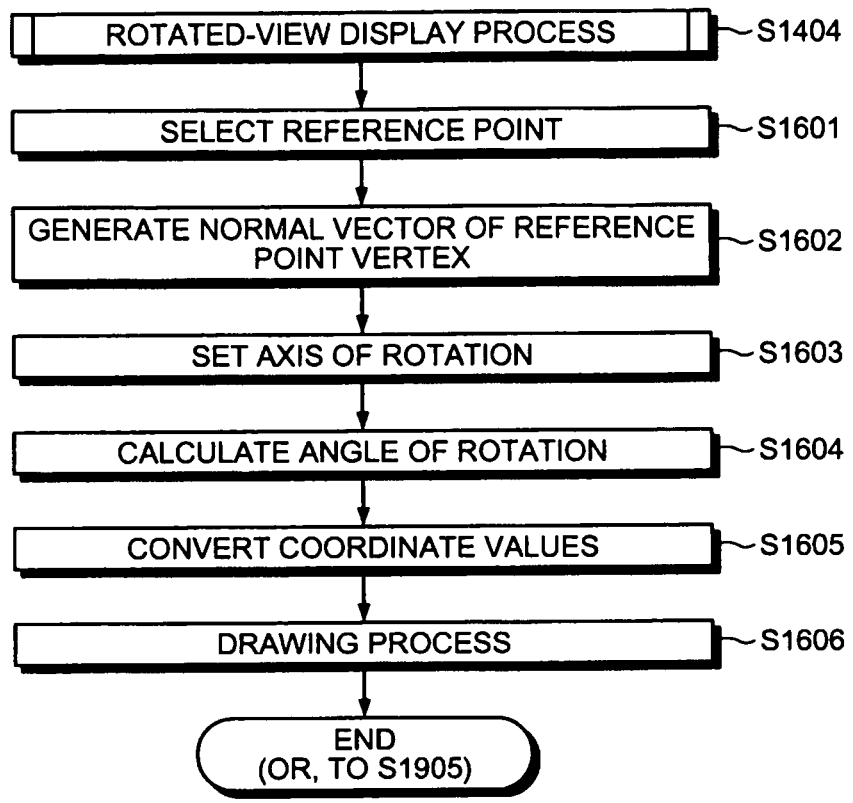
FIG. 16 is a flowchart of a rotated-view display process (step S1404) depicted in the FIG. 14.

FIG. 16 is a flowchart of the rotated-view display process (step S1404) depicted in the FIG. 14. The selecting unit 303 selects the reference point P (step S1601), and the generating unit 304 generates the normal vector of the reference point P vertex (step S1602). The setting unit 305 sets the rotation axis (step S1603), and the angle-of-rotation calculating unit 306 calculates the angle of rotation to point the normal vector of the vertex toward the counter viewing direction vector (step S1604).

The converting unit 307 converts coordinates of the vertices in the display surface structural data, into coordinates the vertices in a state in which the normal vector has been rotated about the rotation axis, by the angle of rotation (step S1605). The drawing unit 308 draws, in color, the display surface Sd after conversion and the electrostatic potential tnereof (step S1606), enabling the display surface Sd to be displayed from a perspective easily viewed by the user.

Thus, in the first embodiment, by cutting out (extracting) the display surface Sd, only the molecular surface S (the display surface Sd) possibly playing a role in binding is selectively displayed. Therefore, although strong electrostatic potential is taken on, the risk of falsely recognizing, as a binding site, a portion having no possibility of being associated with the interaction due to the positional relation with the binding counterpart, can be reduced.

Further, the electrical characteristic of a portion (the display surface Sd near the reference point P) of the molecular surface S having an electrical characteristic of interest can be automatically drawn in a direction of the line of sight of the user. Therefore, the electrical characteristic of a portion of the molecular surface S having a high possibility of being strongly associated with protein binding can be easily observed.

Next, the second embodiment will be described. In the first embodiment, a configuration was described in which one protein (e.g. protein A) is regarded as the display subject and the other protein (e.g., protein B) is regarded as the comparison subject, where the display surface Sd is cut out from the molecular surface S of the display subject and displayed in a rotated state. In contrast, in the second embodiment, the protein (e.g., protein B) regarded as the comparison subject in the first embodiment is regarded as the display subject and the protein (e.g., protein A) regarded as the display subject in the first embodiment is regarded as the comparison subject; the display surface Sd is cut out from the molecular surface S of the display subject and displayed in a rotated state. The distance between the reference points selected based on the amount of characteristics of the vertices forming the respective display surfaces Sd of the proteins is calculated and displayed with the display surface Sd in rotated state. Parts identical to the those of the first embodiment are given the same reference numerals used in the first embodiment and description thereof is omitted.

Figure 17:
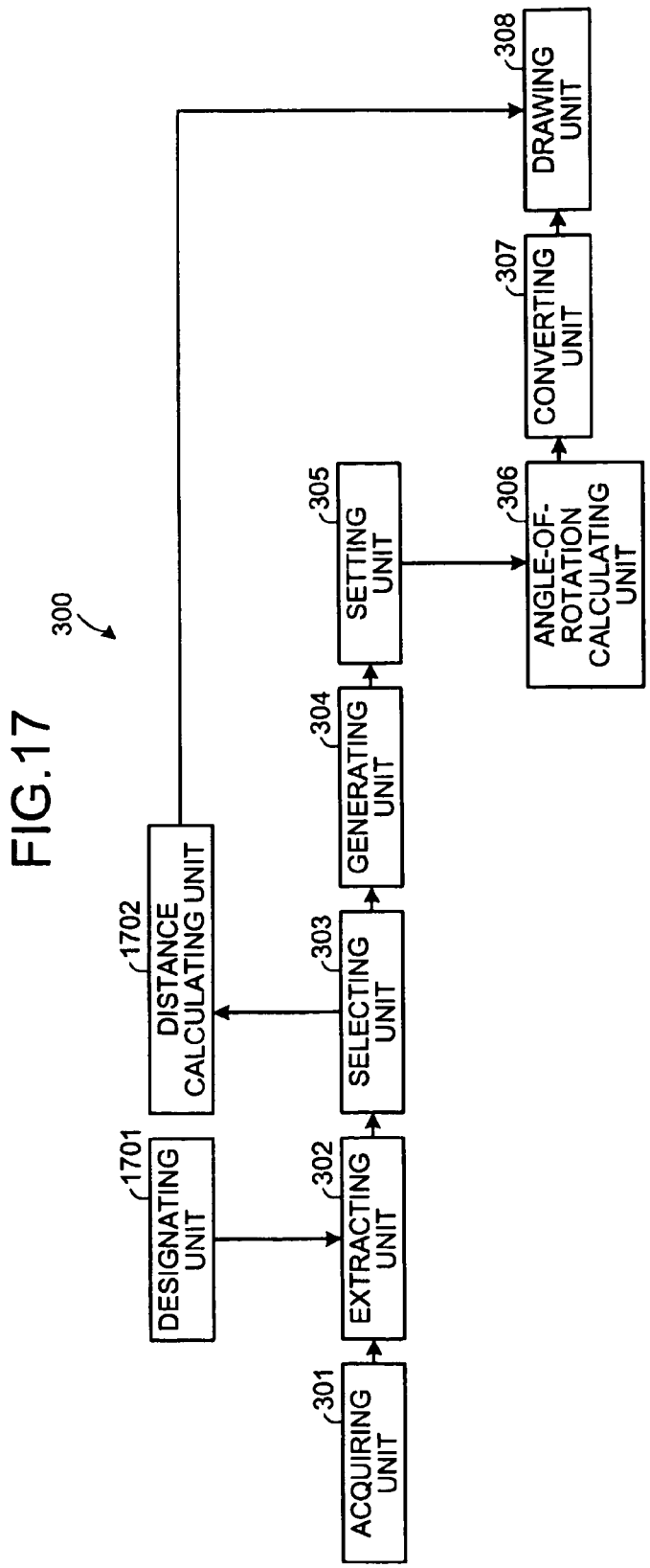
FIG. 17 is a block diagram of a functional configuration of the information display apparatus according to a second embodiment.

FIG. 17 is a block diagram of a functional configuration of the information display apparatus according to the second embodiment. In the second embodiment, includes a designating unit 1701 and a distance calculating unit 1702 in addition to configuration of the first embodiment. Functions of the designating unit 1701 and the distance calculating unit 1702 are also, for example, implemented by executing on the CPU 201, a program stored in a storage device such as the ROM 202, the RAM 203, the magnetic disk 205, and the optical disk 207 depicted in FIG. 2 or by the I/F 209.

The designating unit 1701 has a function of performing a first designation of designating one of the 3-dimensional structural data (e.g., antigen) in an arbitrary 3-dimensional structural data pair as the display subject and the other 3-dimensional structural data (e.g., antibody) as the comparison subject. The designating unit 1701 has a further function of performing a second designation that is opposite to the first designation where the 3-dimensional structural data designated as the comparison subject (antibody) in the first designation is designated as the display subject and the other 3-dimensional structural data (antigen) is designated as the comparison subject.

For example, with respect to a 3-dimensional structural data pair acquired by the acquiring unit 301, the processes from the extracting unit 302 to the drawing unit 308 are performed with the antigen designated as the display subject by the first designation and the processes from the extracting unit 302 to the drawing unit 308 are further performed with the antibody designated as the display subject by the second designation.

In this example, when the first or the second designation is performed, according to the designation, the extracting unit 302 determines/changes the display subject and the comparison subject and then performs the process described in the first embodiment. Consequently, if the 3-dimensional structural data (e.g., antigen) is regarded as the display subject, the display surface Sd therefor can be drawn from a perspective easily viewed by the user and if the other 3-dimensional structural data (e.g., antibody) is regarded as the display subject, the display surface Sd therefor can be drawn from a perspective easily viewed by the user.

The distance calculating unit 1702 has a function of calculating the distance between reference points, i.e., the reference point P1 selected by the selecting unit 303 according to the first designation and the reference point P2 selected by the selecting unit 303 according to the second designation. For example, if the coordinates of the reference point P1 obtained by the first designation in which is the antigen is designated as the display subject are (x1, y1, z1) and the coordinates of the reference point P2 obtained by the second designation in which the antibody is designated as the display subject are (x2, y2, z2), the distance d between the reference points can be calculated by equation 1 below.

$$d=\sqrt{\{(x2-x1)2+(y2-y1)2+(z2-z1)2\}} \qquad (1)$$

At the drawing unit 308, with respect to the display surface Sd displayed in a rotated state, a line connecting the reference point P1 and the reference point P2 is drawn together with the value of the distance d between the reference points.

Figure 18:
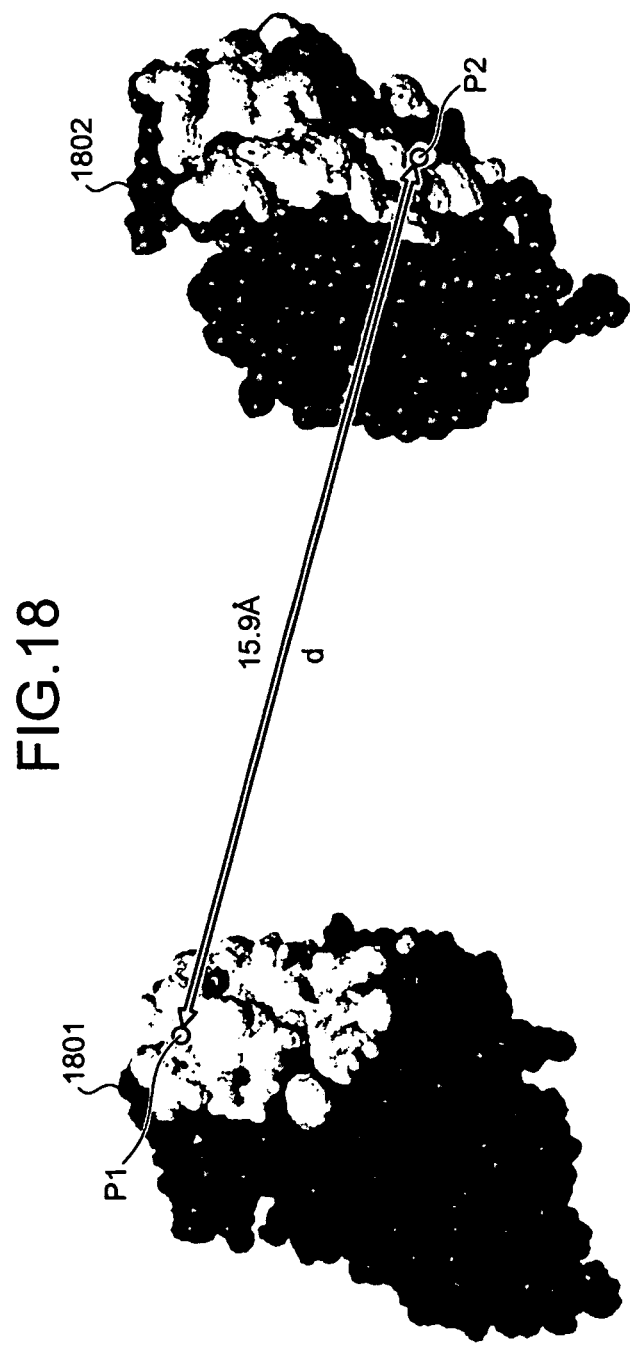
FIG. 18 is a diagram of an example of a 3-dimensional model of a protein displayed in a rotated state according to the second embodiment.

FIG. 18 is a diagram of an example of a 3-dimensional model of the protein displayed in a rotated state according to the second embodiment. In FIG. 18, a 3-dimensional model 1801 of one of the proteins (antibody) and a 3-dimensional model 1802 of the other protein (antigen) are displayed in a rotated state according to the processes of the first embodiment. A line connecting the reference points P1 and P2 as well as the distance d between the reference points is further displayed.

Figure 19:
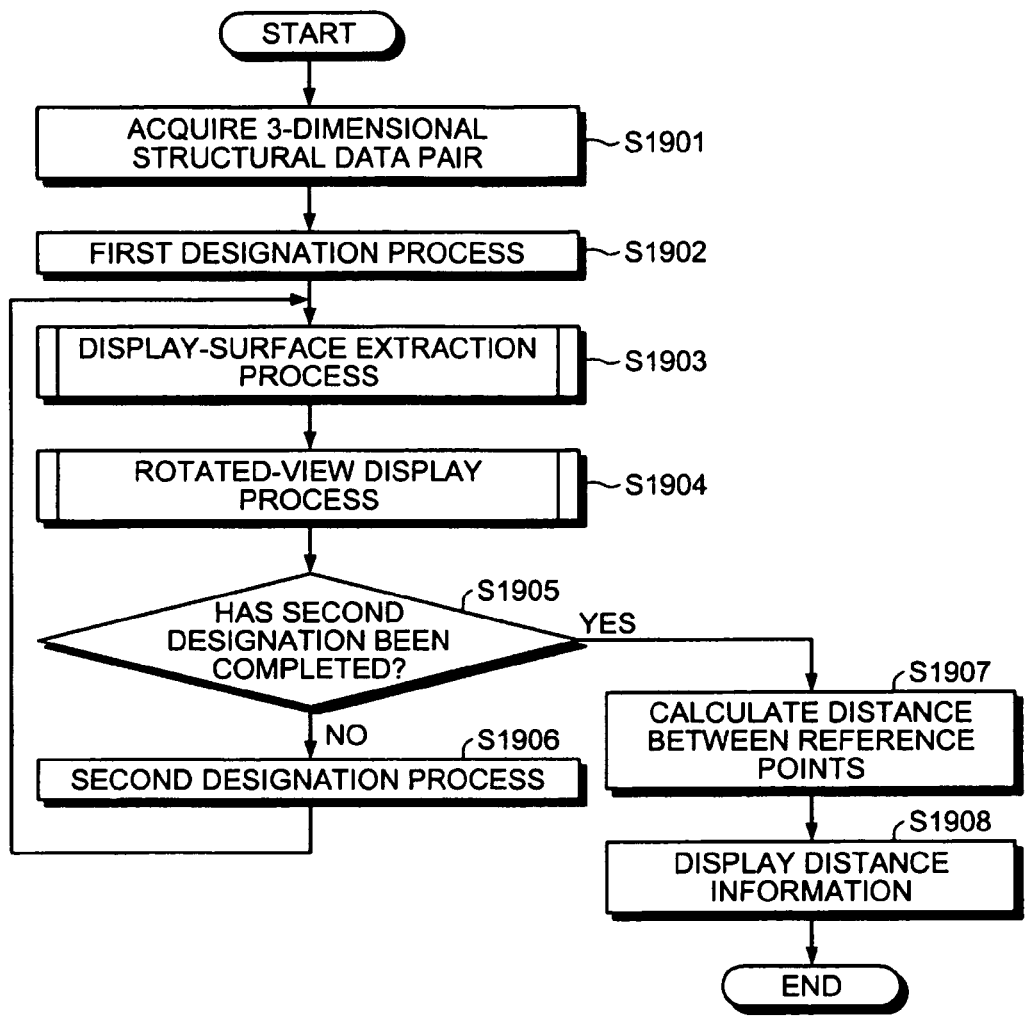
FIG. 19 is a flowchart of an information display process performed by the information display apparatus according to the second embodiment.

FIG. 19 is a flowchart of the information display process performed by the information display apparatus according to the second embodiment.

The acquiring unit 301 acquires a 3-dimensional structural data pair (step S1901) and the designating unit 1701 executes the first designation process (step S1902). Here, for example, the 3-dimensional structural data of the antigen is assumed to be the display subject and the other 3-dimensional structural data (antibody) is assumed to be the comparison subject. Subsequently, the display-surface extraction process (step S1903) and the rotated-view display process (step S1904) are executed with respect to the display subject and the comparison subject designated by the first designation.

The display-surface extraction process (step S1903) is the same process as the display-surface extraction process (step S1403) depicted in FIGS. 14 and 15. The rotated-view display process (step S1904) is the same process as the rotated-view display process (step S1404) depicted in FIGS. 14 and 16.

The information display apparatus determines whether the second designation has been completed (step S1905). If the second designation has not been completed (step S1905: NO), the designating unit 1701 executes the second designation process of inversely designating the proteins designated as the display subject and the comparison subject by the first designation process (step S1906). Here, for example, the 3-dimensional structural data of the antibody designated as the comparison subject at the first designation is designated as the display subject and the other 3-dimensional structural data (antigen) is designated as the comparison subject. Subsequently, the display-surface extraction process (step S1903) and the rotated-view display process (step S1904) are executed with respect to the display subject and the comparison subject designated by the second designation.

At step S1905, if the second designation has been completed (step S1905: YES), the distance calculating unit 1702 calculates the distance between the reference points (step S1907). The drawing unit 308 displays distance information (the value of the distance d between the reference points, an arrow connecting the reference points P1 and P2, etc.) (step S1908).

In this manner, according to the second embodiment, for adjacent constituent proteins, portions of the molecular surfaces S having a high possibility of interacting (vicinities of the respective reference points P) can be displayed opposing one another with the distance therebetween also displayed. Therefore, the user can easily determine whether the possibility of noncovalent interaction is high.

Next the third embodiment will be described. In the third embodiment, multiple 3-dimensional structural data pairs having a common display subject are prepared, one of which is regarded as a 3-dimensional-structural-data reference pair and the remainder of which are regarded as 3-dimensional-structural-data comparison pairs. The respective display surfaces Sd of the 3-dimensional-structural-data reference pair display subject (reference display subject) and the 3-dimensional-structural-data comparison pair display subject (comparison display subject) and having electrical characteristics are displayed collectively to form a perspective view from substantially the same direction. Linked with the 3-dimensional-structural-data reference pair display subject, the 3-dimensional-structural-data comparison pair display subject is displayed in a rotated state.

The present embodiment is useful, for example, in finding a variant antigen that is related to a wild-type antigen that binds with a given antibody and binds more strongly with the antibody. In other words, in such a case, although knowing where each of the antigens binds to the antibody is a large clue in determining the strength of the binding behavior, application of the present embodiment in which the antibody is assumed to be the display subject, makes identification of binding site variations originating from antigen differences and identification of antigens having a high possibility of strongly binding to an important substructure of an antibody, etc. easy.

Hereinafter, the embodiment will be described in detail taking such a case as an example. In the example, the 3-dimensional structural data 400 of a protein complex having an antibody protein and a wild-type antigen protein is assumed as a "3-dimensional-structural-data reference pair" and the 3-dimensional structural data 400 of a protein complex having the same type of antibody protein and a variant antigen protein is assumed as a "3-dimensional-structural-data comparison pair".

The antibody proteins in these 3-dimensional structural data pairs are basically the same protein, however, in general, since proteins that are of the same type do not always have the same amino acid sequence, in the following description, it is assumed that parts of the amino acid sequence of the antibody proteins differ. For example, originating from this assumption, a determining unit 2101 and a searching unit 2102 obtain amino acid sequences common between the reference display subject and the comparison display subjects, and calculate an arrangement position of the comparison display subject so that the substructure corresponding to the common sequence portion overlaps.

In the third embodiment, by displaying the display surfaces Sd and the electrical characteristics thereof with respect to the 3-dimensional structural data pair display subjects (herein, the antibody), binding sites (portions of the display surface Sd of the antibody that has been determined to have a high possibility of noncovalent interaction by the electrical characteristics) when the antigens protein bind with the antibody protein can be viewed from substantially the same perspective all at once.

In other words, for example, if a wild-type antigen has bound (3-dimensional structural reference data) or if a variant antigen has bound (3-dimensional structural comparison data), binding sites on the antibody side and differences in the electrical characteristics in the vicinity of the binding sites are looked at, enabling efficient comparison. Therefore, variations among the binding sites on the antibody protein side, originating from antigen protein differences can be easily identified as well as antigens that have a high possibility of strongly binding with important substructures of the antibody.

FIG. 20 is a diagram of an example of display in a rotated state according to the third embodiment. In FIG. 20, in a first display area 2001 on the left-hand side, 3-a dimensional model reference of the display subject is displayed. Areas of colors other than black are the display surfaces Sd colored according to electrical characteristics. A character string WT on the upper left indicates that the antigen protein that binds to the 3-dimensional model of the display subject is a wild-type antigen. Further, a character string (Lys96) also on the upper left represents a variant portion of an amino acid sequence at the antigen protein that binds to the 3-dimensional model of the display subject.

The display areas 2001 and 2002 depicted in FIG. 20 uses a 3-dimensional viewing coordinate system that assumes the viewpoint depicted in FIG. 1 as the origin 0. The center of mass of the reference display subject is assumed to be a given position along the Z axis.

In the second display area 2002 on the right-hand side, 3-dimensional models of the comparison display subjects are depicted. Areas of colors other than black are the display surfaces Sd colored according to electrical characteristics. Character strings to the upper left of the 3-dimensional models of the comparison display subjects indicate the names of the varied amino acid sequences that are in the amino acid sequence of the antigen proteins that interact with the display subject (antibody). The comparison display subjects are arranged in the same viewing coordinate system as the reference display subject and are displayed in a state depicting rotation by the angle of rotation of the reference display subject. Further, the rotation axis of the reference display subject may be used as the rotation axes of the comparison display subjects or the rotation axes of the comparison display subjects may be obtained from the comparison display subjects. Parts identical to those of the first embodiment are given the same reference numerals used in the first embodiment and description thereof is omitted.

FIG. 21 is a block diagram of a functional configuration of the information display apparatus according to the third embodiment. In the third embodiment, in addition to the functions of the first embodiment, the configuration further includes the determining unit 2101 and the searching unit 2102. Functions of the determining unit 2101 and the searching unit 2102 are also implemented, for example, by executing on the CPU 201, a program stored in a storage device such as the ROM 202, the RAM 203, the magnetic disk 205, and the optical disk 207 depicted in FIG. 2 or by the I/F 209. Although the functions of the acquiring unit 301 to the drawing unit 308 are similar to those of the first embodiment, differing points will be described.

The acquiring unit 301 performs the acquisition process of the first embodiment with respect to the 3-dimensional-structural-data reference pair and the 3-dimensional-structural-data comparison pairs, respectively. The 3-dimensional-structural-data comparison pairs have the same 3-dimensional-structural-data reference pair as the display subject and different comparison subjects.

FIG. 22 is a diagram of 3-dimensional structural data that is for a comparison protein complex and from which the 3-dimensional-structural-data comparison pair is derived. Three-dimensional structural data 2200 of the comparison protein complex includes the same fields depicted in FIG. 4. The 3-dimensional-structural-data reference pair display subject is assumed to be "reference display subject" and the 3-dimensional-structural-data comparison pair display subjects are assumed to be "comparison display subjects".

For example, if the reference display subject is assumed to be the antibody and the comparison subject thereof is assumed to the antigen, the comparison display subject is also the same antibody that is the reference display subject. On the other hand, the comparison subject of the comparison display subject is a variant of the antigen that is the 3-dimensional-structural-data reference pair comparison subject and in which a portion of the amino acid sequence has been substituted. The extracting unit 302, the selecting unit 303, and the generating unit 304 perform the extraction process, the selection process, and the generation process of the first embodiment. Further, as described, although the antibody of the reference display subject and the antibody of the comparison display subject are basically the same protein, as a sequence of amino acids, it is not an issue if portions (portions other than those associated with key functions) differ.

FIG. 23A is a diagram of the molecular-surface structural data that represents the molecular surface S of the antibody that is reference display subject. Molecular-surface structural data 2301 includes the same fields depicted in FIGS. 7A and 7B. FIG. 23B is a diagram of reference point data that indicates the reference point of the molecular surface S of the antibody that is the reference display subject. Reference point data 2302 includes the coordinates of the reference point of the molecular surface S of the antibody that is the reference display subject and the electrostatic potential.

FIG. 24A is a diagram of the molecular-surface structural data representing the molecular surface S of the antibody that is comparison display subject. Molecular-surface structural data 2401 includes the same fields depicted in FIGS. 7A and 7B. FIG. 24B is a diagram of reference point data that indicates the reference point of the molecular surface S of the antibody that is the comparison display subject. Reference point data 2402 includes the coordinates of the reference point of the molecular surface S of the antibody that is the comparison display subject.

The setting unit 305 performs the setting process of the first embodiment. For example, the setting unit 305 obtains a rotation axis for reference display subject as described in the first embodiment. On the other hand, a rotation axis for comparison display subject is not obtained here. Furthermore, the angle-of-rotation calculating unit 306 performs the angle-of-rotation calculation process of the first embodiment only for the reference display subject.

The determining unit 2101 has a function of determining commonalities between sequences of the constituent elements of the reference display subject and sequences of the constituent elements of the comparison display subject. For example, the determining unit 2101 executes multiple sequence alignment on the amino acid sequence of the reference display subject and on the amino acid sequence of the comparison display subject and uses homologous amino acid sequences as partial chains for performing alignment. An existing calculation method such as that described in Larkin, M. A., et al., "Clustal W and Clustal X version 2.0", Bioinformatics, Vol. 23: P. 2947-2948 (2007) is used as the calculation method in the multiple sequence alignment of the amino acid sequences. Although this process is necessary of if the proteins (antibody) of the reference display subject/comparison display subjects are not completely identical, if it can be assured that the proteins are completely identical, the process may be omitted and the entire amino acid sequence may be regarded as a partial chain for performing alignment.

FIG. 25 is diagram of an execution example of multiple sequence alignment. In FIG. 25, "reference" lines are amino acid sequences of the antibody protein of the reference display subject and "comparison" lines are amino acid sequences of the antibody protein of the comparison display subject. Furthermore, "*" in FIG. 25 indicate that at the same position in the line above, the amino acid in the reference display subject and the amino acid in the comparison display subject are the same.

The searching unit 2102 has a function of locating arrangement positions of the comparison display subject with respect to the reference display subject, such that constituent elements determined by the determining unit 2101 to have commonality, overlap. For example, with the center of mass of the reference display subject as the origin, the searching unit 2102, in the 3-dimensional space in which the reference display subject is placed, superimposes the reference display subject and each of the comparison display subjects such that the root mean square deviation (RMSD) between structures of the partial chains for performing the alignment are minimized and locates arrangement positions of the comparison display subject. Although various methods are known for selecting an atom to be used in the RMSD calculation, here, a heavy atom (—N—(C)—CO—) of the main chain of the amino acid sequence forming the partial chain is used.

Figure 26:
FIG. 26 depicts an example of a 3-dimensional model superimposing the comparison subject on the reference display subject.

FIG. 26 depicts an example of a 3-dimensional model superimposing the comparison subject on the reference display subject. In a 3-dimensional model 2600 depicted in FIG. 26, white portions indicate that the reference display subject and the comparison display subject have the same arrangement positions; whereas black portions indicate that the reference display subject and the comparison display subject have different arrangement positions.

The converting unit 307 performs the conversion process of the first embodiment on the reference display subject and the comparison display subject, respectively. For example, the converting unit 307 converts the coordinates of the vertices forming the display surface Sd of the reference display subject into coordinates of the vertices in a state where the normal of the reference point P has been rotated by the angle of rotation calculated by the angle-of-rotation calculating unit 306 and points in the counter viewing direction.

If the arrangement positions of the comparison display subject are the arrangement positions retrieved by the searching unit 2102, the converting unit 307 converts the coordinates of the vertices forming the display surface Sd of the comparison display subject into coordinates of the vertices in a state where the normal of the reference point P has been rotated by the angle of rotation and points in the counter viewing direction. The rotation axis used for the comparison display subject is the rotation axis obtained from the reference display subject. Alternatively, the rotation axis obtained from the reference display subject may be moved parallelly to pass through a given point. For example, if the rotation axis of the reference display subject is set to pass through the center of mass of the reference display subject, similarly for the comparison display subject, the rotation may be set to pass through the center of mass of the comparison display subject; if the rotation axis of the reference display subject is set to pass through the reference point P of the display surface Sd of the reference display subject, similarly the rotation axis of the comparison display subject may also be set to pass through the reference point P of the display surface Sd of the comparison display subject.

Figure 20:
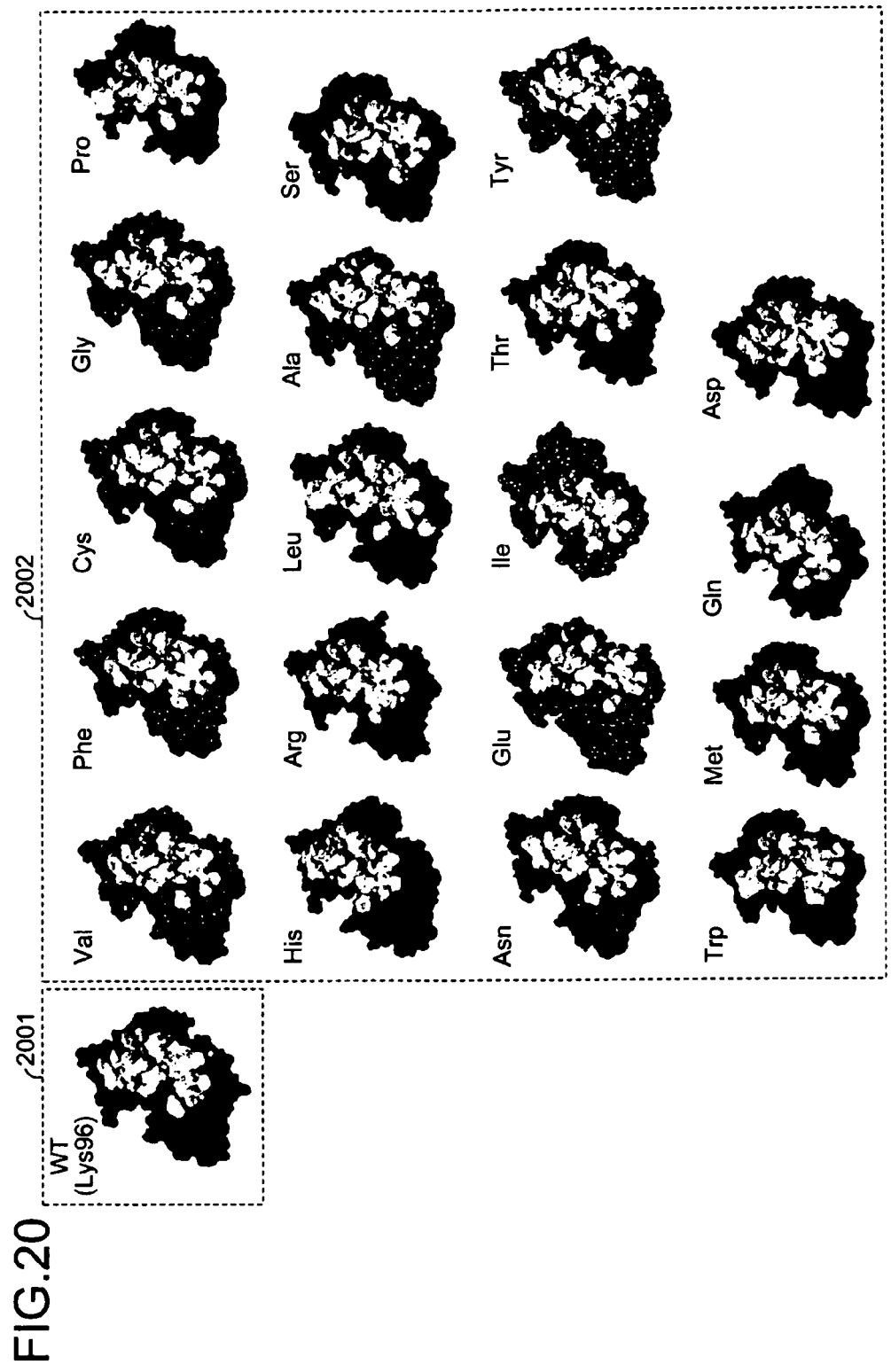
FIG. 20 is a diagram of an example of display in a rotated state according to a third embodiment.
Figure 21:
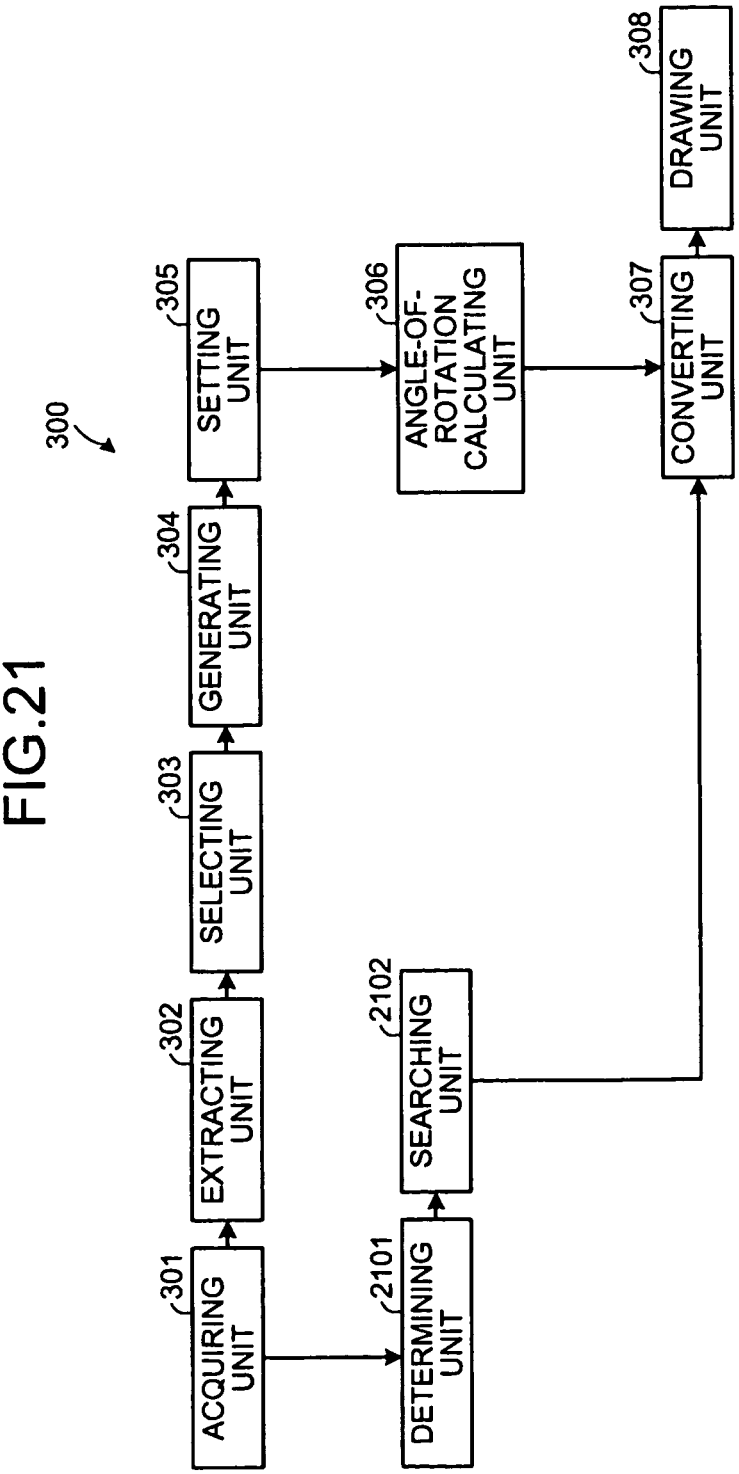
FIG. 21 is a block diagram of a functional configuration of the information display apparatus according to the third embodiment.

The drawing unit 308 performs the drawing process of the first embodiment on the reference display subject and the comparison display subject, respectively. Consequently, similar to the first embodiment, the reference display subject is displayed in a rotated state and linked to the rotation of the reference display subject, the comparison display subject is also displayed in a rotated state. As depicted in FIG. 20, the reference display subject and the comparison display subject are displayed in separate display areas.

Figure 27A:
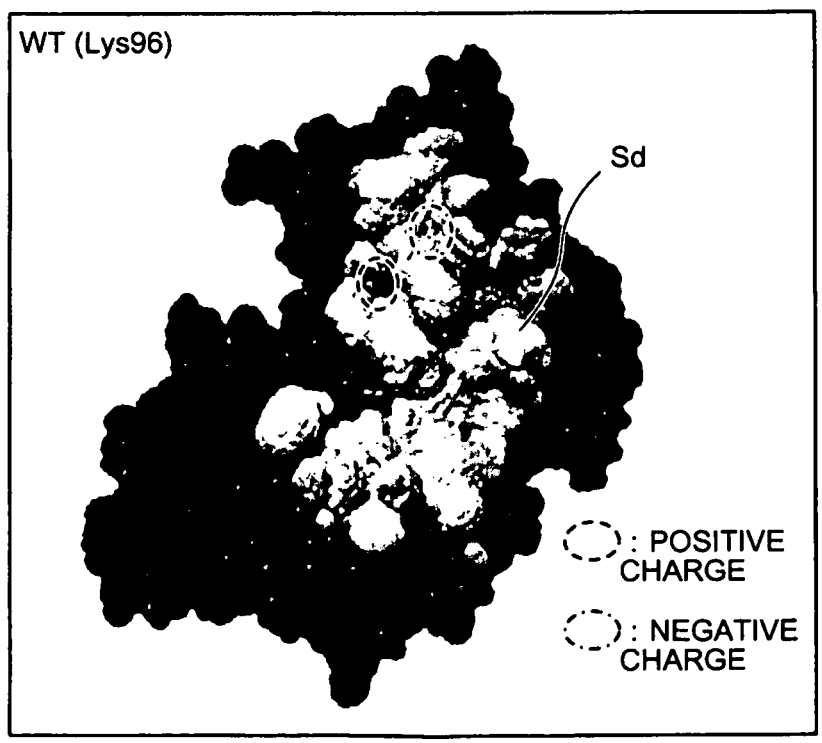
FIG. 27A depicts an example of a rotated 3-dimensional model of a wild-type antibody (reference display subject).
Figure 27B:
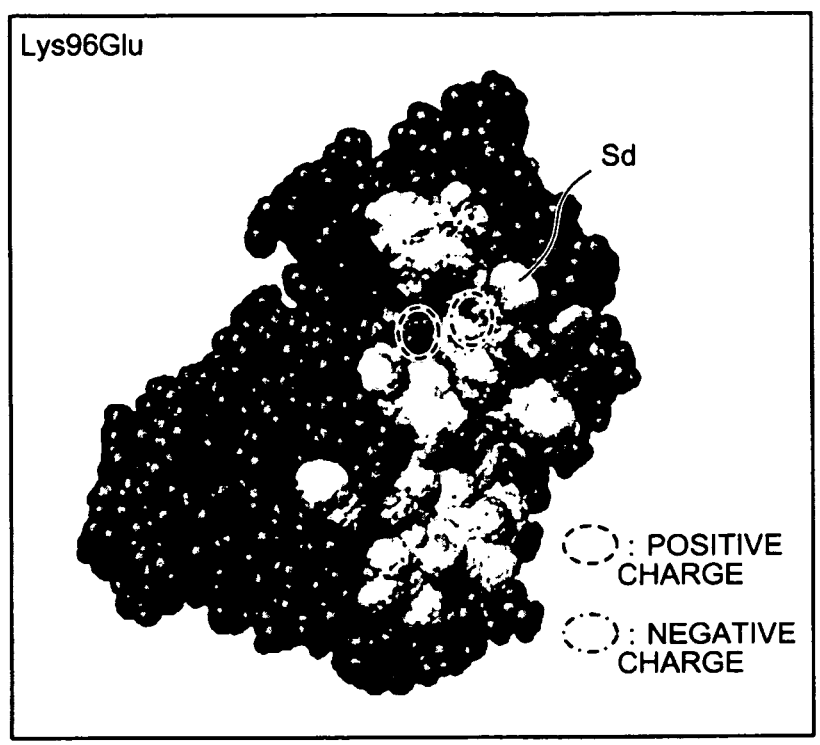
FIG. 27B depicts an example of a rotated 3-dimensional model of an antibody (comparison display subject).

FIG. 27A depicts an example of a rotated 3-dimensional model of a wild-type antibody (reference display subject). FIG. 27B depicts an example of a rotated 3-dimensional model of an antibody (comparison display subject). In FIGS. 27A and 27B, excluding the display surface Sd, the molecular surface is colored in black.

FIG. 28 is a flowchart of the information display process performed by the information display apparatus according to the third embodiment. The acquiring unit 301 acquires a 3-dimensional-structural-data reference pair and a 3-dimensional-structural-data comparison pair (step S2801). The information display apparatus calculates the respective molecular surfaces S from the structural data (step S2802) and determines whether a display subject (display surface Sd) that has yet to be extracted is present (step S2803). If such a display subject is present (step S2803: YES), the information display apparatus selects one display subject (step S2804), executes the display-surface extraction process identical to step S1403 (step S2805), and returns to step S2803.

On the other hand, at step S2803, if no such display subject is present (step S2803: NO), the information display apparatus determines whether a comparison display subject that has yet to be searched is present (step S2806). If a such comparison display subject is present (step S2806: YES), one comparison display subject is selected (step S2807) and the determining unit 2101 executes a determination process (multiple sequence alignment) (step S2808).

The searching unit 2102 locates arrangement positions of the comparison display subject such that the RMSD between structures of the partial chains for performing alignment of the reference display subject and the comparison subject are minimized (step S2809). Consequently, the center of mass of the reference display subject is set as a reference and arrangement positions of the comparison display subject are determined. The information display apparatus returns to step S2806. At step S2806, if no such comparison display subject is present (step S2806: NO), the information display apparatus executes a display-surface-linked rotated-view display process (step S2810), and ends the series of processes.

Figure 29:
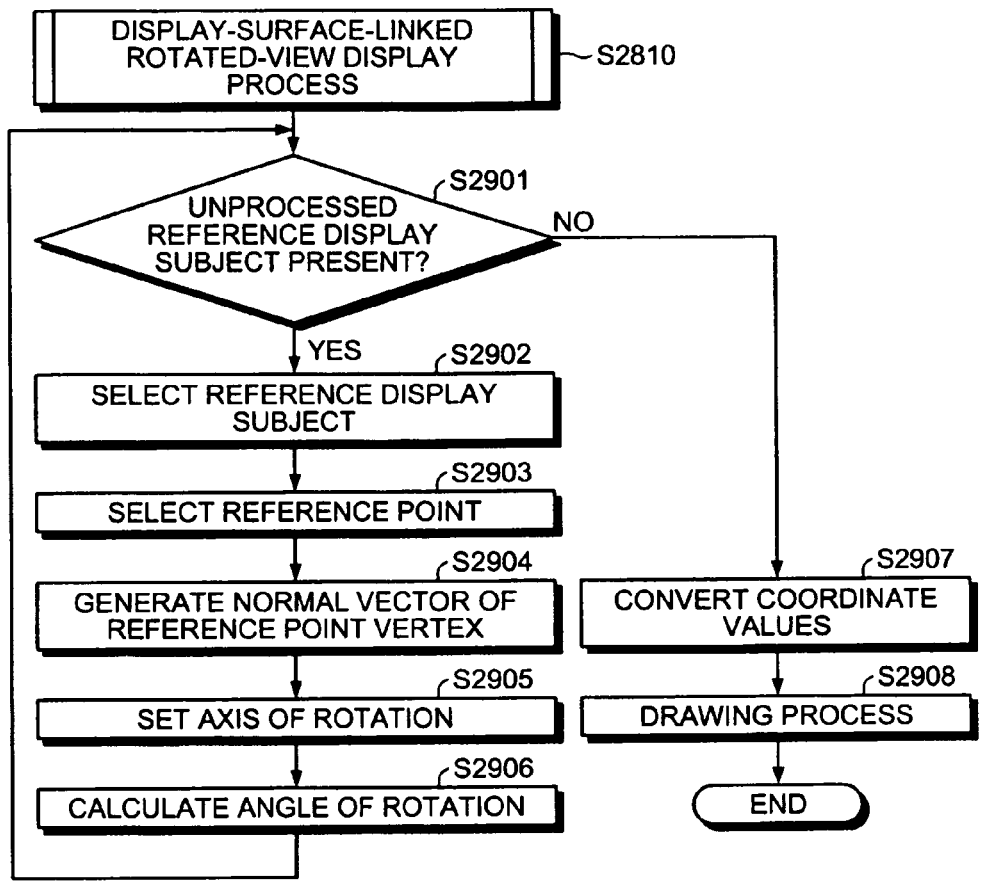
FIG. 29 is a flowchart of a display-surface-linked rotated-view display process (step S2810) depicted in FIG. 28.

FIG. 29 is a flowchart of the display-surface-linked rotated-view display process (step S2810) depicted in FIG. 28. The information display apparatus determines whether an unprocessed reference display subject is present (step S2901). If an unprocessed reference display subject is present (step S2901: YES), the selecting unit 303 selects a reference display subject (step S2902) and similar to the first embodiment, selects a reference point P from among points in the reference display subject (step S2903).

The generating unit 304 generates the normal vector of the reference point P vertex (step S2904) and the setting unit 305 sets the rotation axis (step S2905). Subsequently, the angle-of-rotation calculating unit 306 calculates the angle of rotation (step S2906) and the flow returns to step S2901. At step S2901, if no unprocessed reference display subject is present (step S2901: NO), the converting unit 307 converts the coordinates of the reference display subject in the same manner as described in the first embodiment. Further, the coordinates of the comparison display subject are converted to those corresponding to a state in which the comparison display subject is rotated together with the reference display subject, by the angle of rotation calculated for the reference display subject and about the rotation axis set for the reference display subject (step S2907).

The information display apparatus performs in the respective display areas, the drawing process with respect to the reference display subject and the comparison display subject after the coordinate conversion of the display surface Sd (including the molecular surface S, atoms, and amino acid residue) (step S2908). In this case, the respective display surfaces Sd are colored according to the electrical characteristics of the reference display subject and of the comparison display subject. Other portions of the molecular surface S are monochrome of a given color (black, white, etc.) to emphasize the color of the electric characteristics. Consequently, the display-surface-linked rotated-view display process (step S2810) ends.

Subsequently, by using a pointing device to specify (drag) the rotation direction and the angle of rotation, the reference display subject can be displayed rotated in the specified rotation direction, by the specified angle of rotation. In this case, the converting unit 307 obtains the rotation axis and the angle of rotation, enabling the comparison display subject to be displayed linked to the reference display subject, i.e., rotated in the same direction and by the same angle of rotation. Therefore, the user can view the display subjects from any desired direction, improving user freedom.

In this manner, according to the third embodiment, the electrical characteristics of the display surface Sd (binding site) of the antibody binding to an antigen variant can be viewed all at once from substantially the same direction as the antibody binding to the antigen. Therefore, portions of the binding site of the antibody having large changes in the electrical characteristics by the antigen amino acid variants can be easily identified.

Next, the fourth embodiment will be described. In the first embodiment, based on the characteristic-amounts of the vertices forming the display surface Sd, the normal vector n of the reference point selected from among the vertices is rotated to the counter viewing direction.

In contrast, in the fourth embodiment, the generating unit 304 generates a reference point area, obtains the center of mass of the outer border of the reference point area, and connects the reference point P and the center of mass W to obtain a normal vector c, causing the entire binding area to be displayed.

Figure 30A:
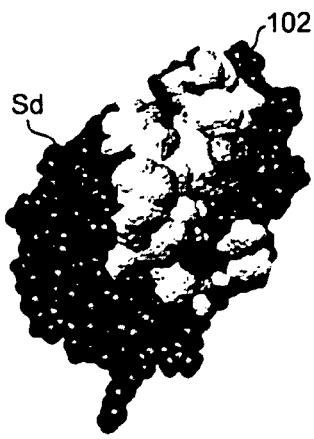
FIG. 30A depicts the display surface of a 3-dimensional antigen model.
Figure 30B:
FIG. 30B depicts a state in which a reference point area has been set.
Figure 30C:
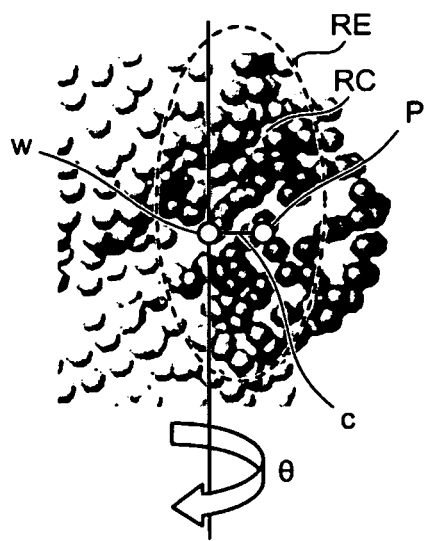
FIG. 30C depicts a state in which a normal vector has been set.

FIGS. 30A, 30B, and 30C depict an example of generation of the normal vector of a reference point on the display surface, using the area (reference point area) formed by the reference point and the surrounding electrostatic potential of the same code, the center of mass of the outer border thereof, and the reference point reference point. FIG. 30A depicts the display surface Sd of the 3-dimensional antigen model 102. FIG. 30B depicts a state in which the reference point area R has been set. The reference point area R is a region that is within the first given distance r1 from the nearest atom and that is formed by a point (e.g., the vertex of a polygon) on the display surface having an electrostatic potential of the same code as the nearest atom.

The distance between the hydrogen donor and recipient of the hydrogen bond is used as the first given distance r1 from the nearest atom. Since the average value is 2.9 to 3.0 [angstrom] according to Kinoshita, K., et al, "eF-site and PDBj-Viewer: database and viewer for protein functional sites", Bioinformatics Vol. 20, No. 8, 2004, pp. 1329-1330, the center value of 2.95 [angstrom] may be used as the first given distance r1.

An inner border area RC is an area inside the reference point area R and within a second given distance r2. If the data particle size for the molecular surface is assumed to be 4 grids/[anstrom2], 2.45 [angstrom] resulting from subtracting 0.5 [angstrom] from r1 is used as the second given distance r2.

An outer border RE of the reference point area R is reference point area R remaining after the inner border area RC has been removed. The center of mass W of the outer border RE of the reference point area R is obtained. Since methods of obtaining the center of mass W are commonly know, detailed description will be omitted. However, as a simple method, the coordinates of the center of mass W can be obtained by averaging the coordinates of the atoms forming the outer border RE of the reference point area R.

FIG. 30C depicts a state in which a normal vector c has been set. The normal vector c is a normal vector that points toward the center of mass W from the reference point P. Here, the reference point P, which is on a convex surface and normal vector c there of are depicted. A normal vector c on a convex surface points toward the interior of the molecule, whereas the normal vector of a reference point on a concave surface points toward the exterior of the molecule.

Figure 31A:
FIG. 31A depicts the rotated state displayed according to the first embodiment.
Figure 31B:
FIG. 31B depicts the rotated state displayed according to a fourth embodiment.

FIGS. 31A and 31B depict the difference between the rotated displays of the first embodiment and the fourth embodiment. FIG. 31A depicts the rotated state displayed according to the first embodiment and FIG. 31B depicts the rotated state displayed according to the fourth embodiment.

In FIG. 31A, since the direction of the normal vector n of the reference point vertex has been converted to the counter viewing direction, the surrounding area of the reference point P on the display surface Sd can be easily viewed. However, some areas away from the reference point P are difficult to view. In FIG. 31B, instead of the normal vector n of the reference point P vector, the direction of the normal vector c of the reference point P is converted to the counter viewing direction, a rotated state in which an overall balance of the display surface Sd is obtained, can be displayed.

Figure 32:
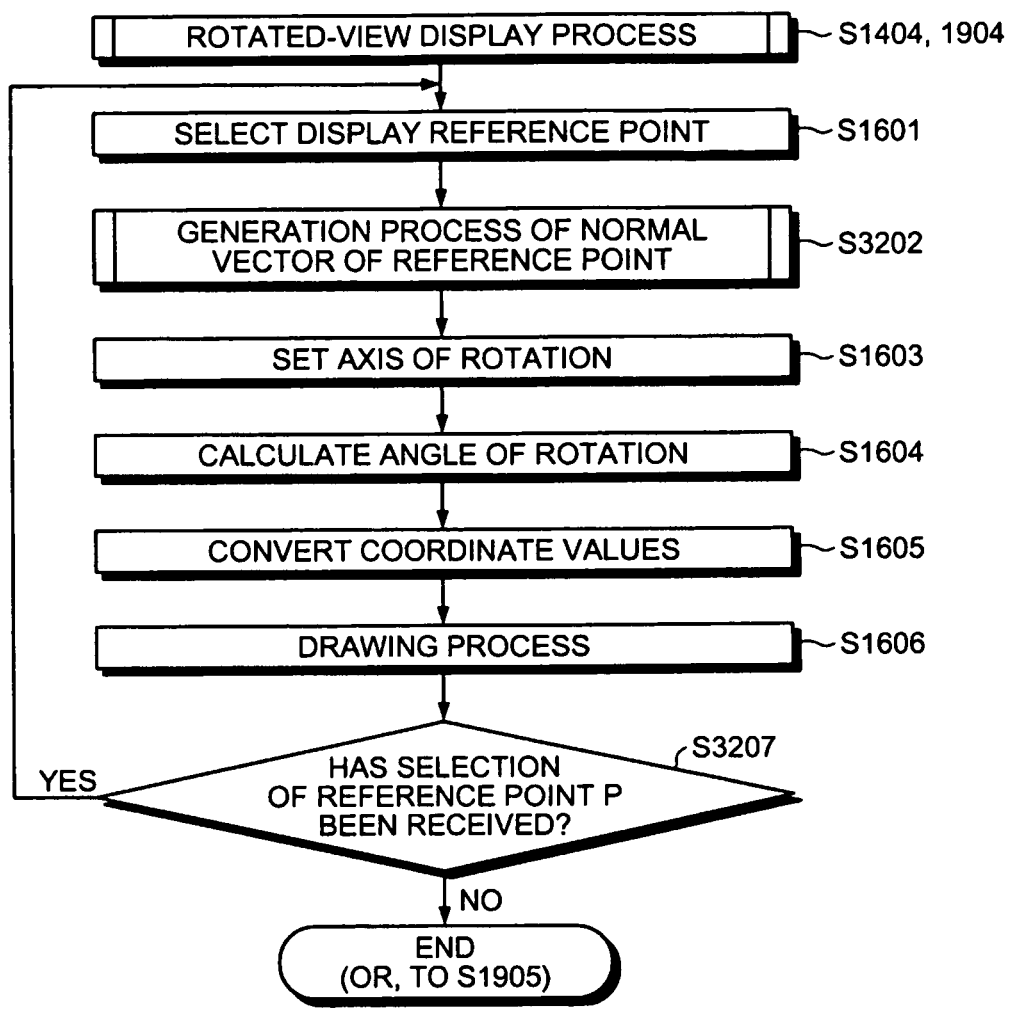
FIG. 32 is a flowchart of the rotated-view display process (step S1404) in FIG. 14 according to the fourth embodiment.
Figure 38:
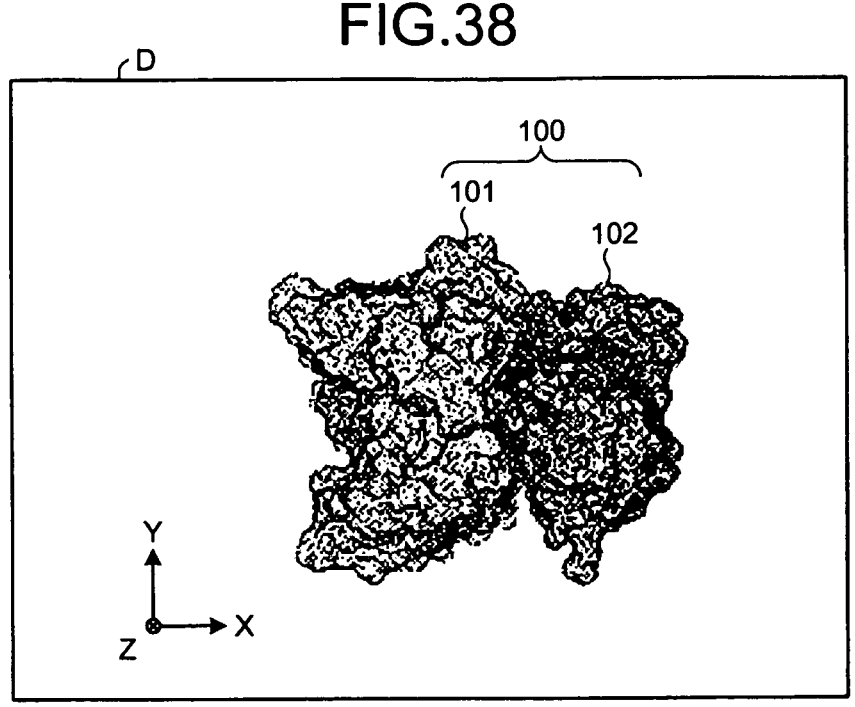
FIG. 38 is diagram of a 3-dimensional model of a protein complex displayed on a display screen.
Figure 39A:
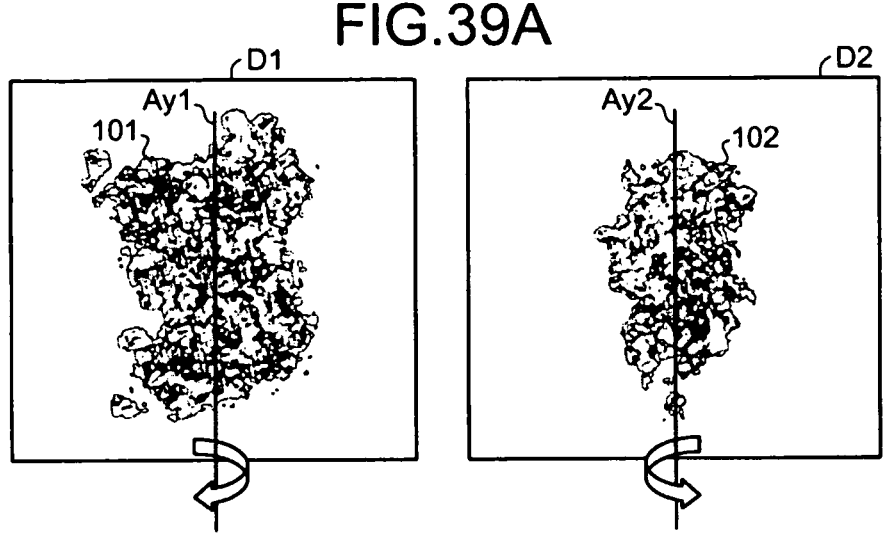
FIGS. 39A and 39B depict the 3-dimensional protein complex model in a rotated state consequent to a user operation.
Figure 39B:
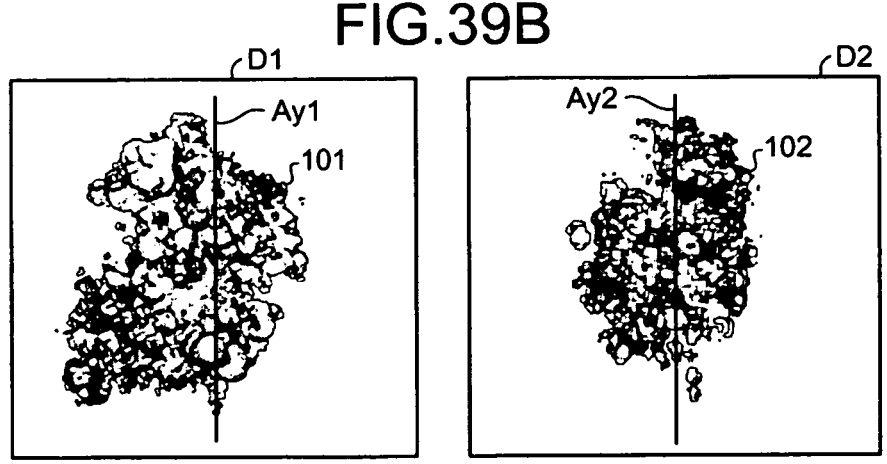

FIG. 32 is a flowchart of the rotated-view display process (step S1404) in FIG. 14 according to the fourth embodiment. In FIG. 32, only differences from FIG. 16 will be described.

In FIG. 32, in place of step S1602 in FIG. 16, a normal vector generation process is executed (step S3202). Consequently, the rotation axis is set (step S1603) and at the calculation of the angle of rotation θ, by obtaining the inner product of the normal vector c of the reference point and the normal vector of the display surface before rotation, the inner product can be obtained as the angle of rotation θ, which is the angle between the normal vector c and the normal vector of the display surface before rotation (step S1604).

After the drawing process (step S1606), the information display apparatus determines whether the selection of the reference point P by a user operation has been newly received (step S3207). If a selection has been received (step S3207: YES), the flow returns to step S1601, the newly selected point is regarded as the reference point and the subsequent processes are executed. On the other hand, if an end instruction has been received (step S3207: NO), the flow transitions to step S1905.

FIG. 33 is a flowchart of the normal vector generation process (step S3202) depicted in FIG. 32. By detecting from the display surface structural data 900 depicted in FIG. 9, a point (atom) that is on the display surface Sd having an electrostatic potential of the same code as the nearest atom of the reference point P and that is within a first given distance r1 from the reference point P, the information display apparatus sets the reference point area R (step S3301). FIG. 34 depicts an example of coordinate data of the reference point area R set at step S3301.

In FIG. 33, by detecting in the reference point area R and from the display surface structural data 900 depicted in FIG. 9, a point (atom) that has an electrostatic potential of the same code as the nearest atom of the reference point P and that is within a second given distance from the reference point P, the information display apparatus sets the inner border area (step S3302). FIG. 35 depicts an example of coordinate data of the inner border area set at step S3302 for the reference point area R.

In FIG. 33, by removing the inner border area from the reference point area R, the outer border of the reference point area R is set (step S3303). FIG. 36 depicts an example of coordinate data of the outer border set at step S3303 for the reference point area R.

Subsequently, in FIG. 33, the information display apparatus calculates the center of mass W of the outer border of the reference point area R (step S3304). FIG. 37 is an example of coordinate data of the center of mass W calculated using the coordinate data of the outer border set at step S3303 for the reference point area R.

Lastly in FIG. 33, the information display apparatus sets a normal vector that passes from the reference point P through the center of mass W (step S3305) and transitions to step S1603. Since the center of mass W of the outer border is not affected by the vertex (including the reference point P) of the inner border area, by connecting the center of mass W and the reference point P, a direction can be identified that couples both the reference point P and the outer border RE. Consequently, by converting the direction of the normal vector c to the counter viewing direction, the rotated state depicted in FIG. 31B can be displayed.

In this manner, in the fourth embodiment, although having strong electrostatic potential, the electrical characteristics of geometrically complimentary (interlocking, etc.) areas having a possibility of being associated with the interaction due to the positional relation with the binding counterpart, can be easily observed.

As described, conventionally, to view electrical characteristics of the molecular surface S related to protein binding, the user has to find binding sites via trial and error by selecting separated constituent proteins that are thought to be associated with binding. Even if a binding site is found, to be easily seen, the viewing direction has to be adjusted.

In the present embodiments, characteristic portions of the display subject surface having a high possibility of being associated with binding with the comparison subject can be displayed in an easily viewable manner. In particular, according to the first embodiment, the molecular surface S (the display surface Sd) having a possibility of playing a role in binding can be selectively displayed alone. Therefore, the risk of falsely recognizing, as a binding site, a portion that although having a strong electrostatic potential, does not have a possibility of being associated with the interaction due to positional relation with the binding counterpart, can be reduced.

The molecular surface S (the molecular surface S in the vicinity of the reference point P) having electrical characteristics of interest and the electrical characteristics thereof can be automatically drawn in a direction of the line of sight of the user. Therefore, the electrical characteristic of a portion of the molecular surface S having a high possibility of being strongly associated with protein binding can be easily observed. In particular, according to the fourth embodiment, at the molecular surface S, although having strong electrostatic potential, the electrical characteristics of geometrically complimentary (interlocking, etc.) areas having a possibility of being associated with the interaction due to the positional relation with the binding counterpart, can be easily observed.

According to the second embodiment, concerning adjacent constituent proteins, portions (the vicinities of the reference point P) of the molecular surface S having a high possibility of being associated with the interaction can be displayed opposed to one another and the distance d between the reference points of the constituent proteins can be displayed. Therefore, the user can easily determine whether the possibility of noncovalent interaction is high. In particular, according to the fourth embodiment, concerning adjacent constituent proteins, the electrical characteristics of geometrically complimentary (interlocking, etc.) areas having a possibility of being associated with the interaction due to the position relation with the binding counterpart on the molecular surface S can be positioned opposing one another and the distance d between the reference points of the constituent proteins can be displayed. Therefore, the user can more easily determine whether the possibility of noncovalent interaction is high.

Further, according to the third embodiment, linked to the reference display subject, the comparison display subjects can be collectively displayed to form a perspective view from substantially the same direction. Therefore, the electrical characteristics (biased charge states in the vicinity of the binding site on an antibody that binds with an antigen variant) of the display surfaces Sd of the comparison display subjects and the electrical characteristics (biased charge states in the vicinity of the binding site of an antibody that binds with a wild-type antigen) of the display surface Sd of the reference display subject can be viewed all at once from substantially the same direction.

Therefore, the user can easily identify position changes of binding sites (portions of the display surface Sd (antibody protein) having strong charge biases suggestive of noncovalent interaction) originating from antigen protein differences, antigens having a high possibility of strongly binding with important antibody substructure (e.g., in a vicinity of a portion of an antibody where wild-type antigen binds), etc.

The information displaying method described in the present embodiment may be implemented by executing a prepared program on a computer such as a personal computer and a workstation. The program is stored on a computer-readable medium such as a hard disk, a flexible disk, a CD-ROM, an MO, and a DVD, read out from the recording medium, and executed by the computer. The program may be distributed through a network such as the Internet. However, the computer-readable medium does not include a transitory medium such as a propagation signal.

According to the embodiments, a characteristic portion of the surface of a display subject having a high possibility of being associated with binding between the display subject and the comparison subject can be displayed in an easily viewable manner.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A non-transitory computer-readable medium storing therein an information display program that causes a computer to execute a process comprising:

acquiring a 3-dimensional structural data pair that includes 3-dimensional structural data for a display subject and 3-dimensional structural data of a comparison subject that is compared to the display subject;

extracting as a display surface of the display subject and from among display subject surfaces identified by the display subject acquired at the acquiring, a surface that is within a given distance from a comparison subject surface identified by the comparison subject;

selecting a reference point from among vertices forming the extracted display surface of the display subject, the selecting being based on the amount of characteristics of the vertices;

generating the normal of the selected reference point;

setting a rotation axis about which the generated normal of the reference point is rotated to point in a counter viewing direction;

calculating based on the normal of the reference point and the normal of the display surface and according to the uneven shape of the display surface, an angle of rotation by which the normal of the reference point is rotated about the rotation axis to point in the counter viewing direction;

converting coordinates of the vertices into coordinates of the vertices in a state where the normal of the reference point has been rotated by the calculated angle of rotation and points in the counter viewing direction; and drawing on a display screen and based on the amount of characteristics, the display surface of the display subject, from a viewing direction subsequent to conversion at the converting.

2. The non-transitory computer-readable medium according to claim 1, the process further comprising:

extracting as a reference point area centered about the selected reference point, a group of vertices having a code identical to that of the reference point on the display surface;

calculating an inner border of the reference point area, the inner border being within a given distance from the reference point;

calculating an outer border of the reference point area by subtracting the inner border from the reference point area; and calculating center of mass of the outer border of the reference point area, wherein the generating includes generating the normal of the reference point by connecting the reference point to the center of mass of the reference point area.

3. The non-transitory computer-readable medium according to claim 1, the process further comprising:

designating among the 3-dimensional structural data pair, a first 3-dimensional structural data to be the display subject and a second 3-dimensional structural data to be the comparison subject in a first designation and further designating the first 3-dimensional structural data to be the comparison subject and the second 3-dimensional structural data to be the display subject in a second designation; and calculating the distance between the reference point selected for the first designation and the reference point selected for the second designation, wherein the drawing includes drawing the display surface of the display subject designated in the first designation and the display surface of the display subject designated in the second designation in correlation with the calculated distance between the reference points.

4. A non-transitory computer-readable medium storing therein an information display program that causes a computer to execute a process comprising:
  acquiring 3-dimensional structural data pairs that include a 3-dimensional-structural-data reference pair that includes 3-dimensional structural data for a display subject and for a comparison subject, and a 3-dimensional-structural-data comparison pair that includes 3-dimensional structural data for the display subject and for a comparison subject that is different from the comparison subject;
  extracting for each of the acquired 3-dimensional structural data pairs, as a display surface of the display subject and from among surfaces of the display subject identified by the display subject, a surface that is within a given distance from a surface of each of the comparison subjects, identified by the comparison subjects;
  determining commonality between arrangement of constituent elements forming a reference display subject that is the display subject of the 3-dimensional-structural-data reference pair and arrangement of constituent elements forming a comparison display subject that is the display subject of the 3-dimensional-structural-data comparison pair;
  locating arrangement positions of the comparison display subject with respect to the reference display subject such that the constituent elements determined to have commonality overlap;
  selecting a reference point from among vertices forming the display surface of the extracted reference display subject and based on the amount of characteristics of each of the vertices;
  generating the normal of the selected reference point of the reference display subject;
  setting a rotation axis that is for the reference display subject and about which the generated normal of the reference point of the reference display subject rotates to point in a counter viewing direction;
  calculating based on the normal of the reference point of the reference display subject and the normal of the display surface of the reference display subject and according to the uneven shape of the display surface of the reference display subject, an angle of rotation by which the normal of the reference point of the reference display subject is rotated about the set rotation axis;
  converting coordinates of the vertices forming the display surface of the reference display subject, into coordinates of the vertices in state where the normal of the reference point has been rotated by the calculated angle of rotation and points in the counter viewing direction and when arrangement positions of the comparison display subject are located as the arrangement positions, converting the coordinates of the vertices forming the display surface of the comparison display subject, into coordinates of the vertices in a state where the normal of the reference point has been rotated by the angle of rotation and points in the counter viewing direction; and
  drawing on a display screen and based on the amounts of characteristics, the display surface of the reference display subject and the display surface of the comparison display subject, after the converting.

5. An information display apparatus comprising:
  an acquiring unit that acquires a 3-dimensional structural data pair that includes 3-dimensional structural data for a display subject and 3-dimensional structural data of a comparison subject that is compared to the display subject;
  an extracting unit that extracts as a display surface of the display subject and from among display subject surfaces identified by the display subject acquired by the acquiring unit, a surface that is within a given distance from a comparison subject surface identified by the comparison subject;
  a selecting unit that selects a reference point from among vertices forming the extracted display surface of the display subject, the selecting being based on the amount of characteristics of the vertices;
  generating unit that generates the normal of the selected reference point;
  a setting unit that sets a rotation axis about which the generated normal of the reference point is rotated to point in a counter viewing direction;
  an angle-of-rotation calculating unit that based on the normal of the reference point and the normal of the display surface and according to the uneven shape of the display surface, calculates an angle of rotation by which the normal of the reference point is rotated about the rotation axis to point in the counter viewing direction;
  a converting unit that converts coordinates of the vertices into coordinates of the vertices in a state where the normal of the reference point has been rotated by the calculated angle of rotation and points in the counter viewing direction; and
  a drawing unit that draws on a display screen and based on the amount of characteristics, the display surface of the display subject, from a viewing direction subsequent to conversion at the converting.

6. The information display apparatus according to claim 5, further comprising:
  an extracting unit that extracts as a reference point area centered about the selected reference point, a group of vertices having a code identical to that of the reference point on the display surface;
  an inner border calculating unit that calculates an inner border of the reference point area, the inner border being within a given distance from the reference point;
  an outer border calculating unit that calculates an outer border of the reference point area by subtracting the inner border from the reference point area; and
  a center-of-mass calculating unit that calculates center of mass of the outer border of the reference point area, wherein
  the generating unit further generates the normal of the reference point by connecting the center of mass to the reference point.

7. The information display apparatus according to claim 6, further comprising:
  a designating unit that among the 3-dimensional structural data pair, designates a first 3-dimensional structural data to be the display subject and a second 3-dimensional structural data to be the comparison subject in a first designation and further designates the first 3-dimensional structural data to be the comparison subject and the second 3-dimensional structural data to be the display subject in a second designation; and
  a distance calculating unit that calculates the distance between the reference point selected for the first designation and the reference point selected for the second designation, wherein
  the drawing unit draws the display surface of the display subject designated in the first designation and the display surface of the display subject designated in the second designation in correlation with the calculated distance between the reference points.

8. An information display apparatus comprising:
an acquiring unit that acquires 3-dimensional structural data pairs that include a 3-dimensional-structural-data reference pair that includes 3-dimensional structural data for a display subject and for a comparison subject, and a 3-dimensional-structural-data comparison pair that includes 3-dimensional structural data for the display subject and for a comparison subject that is different from the comparison subject;
an extracting unit that for each of the acquired 3-dimensional structural data pairs, as a display surface of the display subject and from among surfaces of the display subject identified by the display subject, extracts a surface that is within a given distance from a surface of each of the comparison subjects, identified by the comparison subjects;
a determining unit that determines commonality between arrangement of constituent elements forming a reference display subject that is the display subject of the 3-dimensional-structural-data reference pair and arrangement of constituent elements forming a comparison display subject that is the display subject of the 3-dimensional-structural-data comparison pair;
a searching unit that locates arrangement positions of the comparison display subject with respect to the reference display subject such that the constituent elements determined to have commonality overlap;
a selecting unit that selects a reference point from among vertices forming the display surface of the extracted reference display subject and based on the amount of characteristics of each of the vertices;
a generating unit that generates the normal of the selected reference point of the reference display subject;
a setting unit that sets a rotation axis that is for the reference display subject and about which the generated normal of the reference point of the reference display subject rotates to point in a counter viewing direction;
an angle-of-rotation calculating unit that based on the normal of the reference point and the normal of the display surface and according to the uneven shape of the display surface of the reference display subject, calculates an angle of rotation by which the normal of the reference point of the reference display subject is rotated about the set rotation axis, to point in the counter viewing direction;
a converting unit that converts coordinates of the vertices forming the display surface of the reference display subject, into coordinates of the vertices in state where the normal of the reference point has been rotated by the calculated angle of rotation and points in the counter viewing direction and when arrangement positions of the comparison display subject are located as the arrangement positions, the converting unit converts the coordinates of the vertices forming the display surface of the comparison display subject, into coordinates of the vertices in a state where the normal of the reference point has been rotated by the angle of rotation and points in the counter viewing direction; and
a drawing unit that draws on a display screen and based on the amounts of characteristics, the display surface of the reference display subject and the display surface of the comparison display subject, after the converting.

9. An information display method executed by a computer, the information display method comprising:

acquiring a 3-dimensional structural data pair that includes 3-dimensional structural data for a display subject and 3-dimensional structural data of a comparison subject that is compared to the display subject;
extracting as a display surface of the display subject and from among display subject surfaces identified by the display subject acquired at the acquiring, a surface that is within a given distance from a comparison subject surface identified by the comparison subject;
selecting a reference point from among vertices forming the extracted display surface of the display subject, the selecting being based on the amount of characteristics of the vertices;
generating the normal of the selected reference point;
setting a rotation axis about which the generated normal of the reference point is rotated to point in a counter viewing direction;
calculating based on the normal of the reference point and the normal of the display surface and according to the uneven shape of the display surface, an angle of rotation by which the normal of the reference point is rotated about the rotation axis to point in the counter viewing direction;
converting coordinates of the vertices into coordinates of the vertices in a state where the normal of the reference point has been rotated by the calculated angle of rotation and points in the counter viewing direction; and
drawing on a display screen and based on the amount of characteristics, the display surface of the display subject, from a viewing direction subsequent to conversion at the converting.

10. The information display method according to claim 9, further comprising:
extracting as a reference point area centered about the selected reference point, a group of vertices having a code identical to that of the reference point on the display surface;
calculating an inner border of the reference point area, the inner border being within a given distance from the reference point;
calculating an outer border of the reference point area by subtracting the inner border from the reference point area; and
calculating center of mass of the outer border of the reference point area, wherein
the generating includes generating the normal of the reference point by connecting the reference point to the center of mass of the reference point area.

11. The information display method according to claim 10, further comprising:
designating among the 3-dimensional structural data pair, a first 3-dimensional structural data to be the display subject and a second 3-dimensional structural data to be the comparison subject in a first designation and further designating the first 3-dimensional structural data to be the comparison subject and the second 3-dimensional structural data to be the display subject in a second designation; and
calculating the distance between the reference point selected for the first designation and the reference point selected for the second designation, wherein
the drawing includes drawing the display surface of the display subject designated in the first designation and the display surface of the display subject designated in the second designation in correlation with the calculated distance between the reference points.

12. An information display method executed by a computer, the information display method comprising:

acquiring 3-dimensional structural data pairs that include a 3-dimensional-structural-data reference pair that includes 3-dimensional structural data for a display subject and for a comparison subject, and a 3-dimensional-structural-data comparison pair that includes 3-dimensional structural data for the display subject and for a comparison subject that is different from the comparison subject;

extracting for each of the acquired 3-dimensional structural data pairs, as a display surface of the display subject and from among surfaces of the display subject identified by the display subject, a surface that is within a given distance from a surface of each of the comparison subjects, identified by the comparison subjects;

determining commonality between arrangement of constituent elements forming a reference display subject that is the display subject of the 3-dimensional-structural-data reference pair and arrangement of constituent elements forming a comparison display subject that is the display subject of the 3-dimensional-structural-data comparison pair;

locating arrangement positions of the comparison display subject with respect to the reference display subject such that the constituent elements determined to have commonality overlap;

selecting a reference point from among vertices forming the display surface of the extracted reference display subject and based on the amount of characteristics of each of the vertices;

generating the normal of the selected reference point of the reference display subject;

setting a rotation axis that is for the reference display subject and about which the generated normal of the reference point of the reference display subject rotates to point in a counter viewing direction;

calculating based on the normal of the reference point and the normal of the display surface and according to the uneven shape of the display surface of the reference display subject, an angle of rotation by which the normal of the reference point of the reference display subject is rotated about the set rotation axis, to point in the counter viewing direction;

converting coordinates of the vertices forming the display surface of the reference display subject, into coordinates of the vertices in state where the normal of the reference point has been rotated by the calculated angle of rotation and points in the counter viewing direction and when arrangement positions of the comparison display subject are located as the arrangement positions, converting the coordinates of the vertices forming the display surface of the comparison display subject, into coordinates of the vertices in a state where the normal of the reference point has been rotated by the angle of rotation and points in the counter viewing direction; and drawing on a display screen and based on the amounts of characteristics, the display surface of the reference display subject and the display surface of the comparison display subject, after the converting.

* * * * *